(12) United States Patent
Duncan et al.

(10) Patent No.: US 9,896,422 B2
(45) Date of Patent: *Feb. 20, 2018

(54) TETRACYCLINE DERIVATIVES WITH REDUCED ANTIBIOTIC ACTIVITY AND NEUROPROTECTIVE BENEFITS

(71) Applicant: Neumedics, Seattle, WA (US)

(72) Inventors: Iain W. Duncan, Seattle, WA (US); Edward A. Kesicki, Bothell, WA (US); Carl G. Osborne, Lovettsville, VA (US); William D. Schwieterman, Mobil, AL (US); Irina Jacobson, Sammamish, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/427,235

(22) Filed: Feb. 8, 2017

(65) Prior Publication Data

US 2017/0144979 A1    May 25, 2017

Related U.S. Application Data

(63) Continuation of application No. 14/860,803, filed on Sep. 22, 2015, now Pat. No. 9,573,912, which is a continuation of application No. 13/714,052, filed on Dec. 13, 2012, now Pat. No. 9,168,265, which is a continuation of application No. 12/501,202, filed on Jul. 10, 2009, now Pat. No. 8,338,477.

(60) Provisional application No. 61/080,114, filed on Jul. 11, 2008.

(51) Int. Cl.
| | |
|---|---|
| C07D 265/34 | (2006.01) |
| C07D 263/52 | (2006.01) |
| A61K 31/423 | (2006.01) |
| A61K 31/536 | (2006.01) |
| A61K 45/06 | (2006.01) |
| C07C 323/60 | (2006.01) |
| C07D 263/62 | (2006.01) |
| C07D 498/10 | (2006.01) |
| A61K 31/65 | (2006.01) |
| C07C 233/58 | (2006.01) |

(52) U.S. Cl.
CPC .......... *C07D 265/34* (2013.01); *A61K 31/423* (2013.01); *A61K 31/536* (2013.01); *A61K 31/65* (2013.01); *A61K 45/06* (2013.01); *C07C 233/58* (2013.01); *C07C 323/60* (2013.01); *C07D 263/52* (2013.01); *C07D 263/62* (2013.01); *C07D 498/10* (2013.01); *C07C 2603/46* (2017.05)

(58) Field of Classification Search
CPC .......................... C07D 265/34; C07D 263/52
See application file for complete search history.

(56) References Cited

U.S. PATENT DOCUMENTS

| | | |
|---|---|---|
| 4,904,475 A | 2/1990 | Gale et al. |
| 5,656,286 A | 8/1997 | Miranda et al. |
| 5,789,395 A | 8/1998 | Amin et al. |
| 5,834,450 A | 11/1998 | Su |
| 5,919,775 A | 7/1999 | Amin et al. |
| 6,140,069 A | 10/2000 | Wardlaw |
| 6,504,080 B1 | 1/2003 | Van Der Putten |
| 6,506,740 B1 | 1/2003 | Ashley et al. |
| 6,613,756 B2 | 9/2003 | Duncan et al. |
| 6,638,922 B2 | 10/2003 | Ashley et al. |
| 6,946,453 B2 | 9/2005 | Ashley et al. |
| 7,056,902 B2 | 6/2006 | Nelson et al. |
| 7,094,806 B2 | 8/2006 | Nelson et al. |
| 7,176,225 B2 | 2/2007 | Sum et al. |
| 7,202,235 B2 | 4/2007 | Levy et al. |
| 7,208,482 B2 | 4/2007 | Garcia-Luzon et al. |
| 2002/0022608 A1 | 2/2002 | Duncan et al. |
| 2003/0092683 A1 | 5/2003 | Du et al. |
| 2003/0186946 A1 | 10/2003 | Cooper et al. |
| 2003/0203881 A1 | 10/2003 | Duncan |
| 2004/0127471 A1 | 7/2004 | Reisberg |
| 2004/0214800 A1 | 10/2004 | Levy et al. |
| 2005/0026876 A1 | 2/2005 | Nelson et al. |
| 2005/0143352 A1 | 6/2005 | Nelson et al. |
| 2005/0282787 A1 | 12/2005 | Myers et al. |
| 2005/0288262 A1 | 12/2005 | Bandarage et al. |
| 2006/0003971 A1 | 1/2006 | Nelson |
| 2006/0089336 A1 | 4/2006 | Nelson et al. |
| 2006/0148766 A1 | 7/2006 | Suh et al. |

(Continued)

FOREIGN PATENT DOCUMENTS

| | | |
|---|---|---|
| WO | 9626926 A1 | 9/1996 |
| WO | 0220022 A1 | 3/2002 |

(Continued)

OTHER PUBLICATIONS

Jittiwud Lertvorachon, et al., "1,12-Substituted tetracyclines as antioxidant agents," Bioorganic & Medicinal Chemistry, 2005, vol. 13, 4627-4637.
Xin Wang, et al., "Minocycline inhibits caspase-independent and-dependent mitochondrial cell death pathways in models of Huntington's disease," PNAS, Sep. 2, 2003, vol. 100, No. 18, 10483-10487.
Yan Yang, et al., "Ectopic Cell Cycle Events Link Human Alzheimer's Disease and Amyloid Precursor Protein Transgenic Mouse Models," J. of Neuroscience, Jan. 18, 2006, vol. 26, No. 3, 775-784.
Sean R. Connell, et al., "Ribosomal Protection Proteins and Their Mechanism of Tetracycline Resistance," Antimicrobial Agents and Chemotherapy, Dec. 2003, vol. 47, No. 12, 3675-3681.

(Continued)

*Primary Examiner* — Sahar Javanmard
(74) *Attorney, Agent, or Firm* — Sherbina Intellectual Property Law, PLLC; Nicholas V. Sherbina

(57) ABSTRACT

The present disclosure is directed to compositions and methods which utilize the tetracycline scaffold, preferably the scaffold of tetracycline or minocycline, and which significantly lack antibiotic activity. The compounds have neuroprotective attributes without interfering with the drugs capacity to pass through the blood brain barrier. These compounds have neuroprotective activity because of their inhibition of neuronal cell cycle progression. The compounds are characterized in part by a fifth ring joining positions 9 and 10.

20 Claims, 3 Drawing Sheets

(56) References Cited

U.S. PATENT DOCUMENTS

| | | |
|---|---|---|
| 2006/0166945 A1 | 7/2006 | Abato et al. |
| 2006/0166946 A1 | 7/2006 | Nelson et al. |
| 2006/0194773 A1 | 8/2006 | Levy et al. |
| 2007/0032496 A1 | 2/2007 | Hergenrother et al. |
| 2007/0093455 A1 | 4/2007 | Abato et al. |
| 2008/0064667 A1 | 3/2008 | Sum et al. |

FOREIGN PATENT DOCUMENTS

| | | |
|---|---|---|
| WO | 03005971 A2 | 1/2003 |
| WO | 2004038000 A2 | 5/2004 |
| WO | 2004064728 A2 | 8/2004 |
| WO | 2005082860 A1 | 9/2005 |
| WO | 2007133798 A2 | 11/2007 |

OTHER PUBLICATIONS

Hideaki Hara, et al., "Inhibition of interleukin 1B converting enzyme family proteases reduces ischemic and excitotixic neuronal damage," PNAS, Mar. 1997, vol. 94, 2007-2012.

Jie Shen, et al., "The presenilin hypothesis of Alzheimer's disease: Evidence for a loss-of-function pathogenic mechanism," PNAS, Jan. 9, 2007, vol. 104, No. 2, 403-409.

Conrad C. Alano, et al., "Minocycline inhibits poly(ADP-ribose) polymerase-1 at nanomolar concentrations," PNAS, Jun. 20, 2006, vol. 103, No. 25, 9685-9690.

Johan Widenfalk, et al., "Neurotrophic Factors and Receptors in the Immature and Adult Spinal Cord after Mechanical Injury or Kainic Acid," J. of Neuroscience, May 15, 2001, vol. 21, No. 10, 3457-3475.

A. Blesch, et al., "Leukemia Inhibitory Factor Augments Neurotrophin Expression and Corticospinal Axon Growth after Adult CNS Injury," J. of Neuroscience, May 1, 1999, vol. 19 No. 9 3556-3566.

Palwinder K. Mander, et al., "Microglia Proliferation Is Regulated by Hydrogen Peroxide from NADPH Oxidase," Journal of Immunology, 2006, vol. 176, 1046-1052.

M. L. Block, et al., "Potent regulation of microglia-derived oxidative stress and dopaminergic neuron survival: substance P vs. dynorphin," FASEB Journal, 2006, vol. 20, 251-258.

Wenming Li, et al., Novel Dimeric Acetylcholinesterase Inhibitor Bis(7)-tacrine, but Not Donepezil, Prevents Glutamate-induced Neuronal Apoptosis by Blocking N-Methyl-D-asparatate Receptors, J. of Biol. Chem., May 6, 2005, vol. 280, No. 18, 18179-18188.

Hong Yang, et al., "MAP Kinase-Independent Signaling in Angiotensin II Regulation of Neuromodulation in SHR Neurons," Hypertension, 1998, vol. 32, 473-481.

Chitkala Satyanarayana, et al., "DRF 3 I 88 a novel semi-synthetic analog of andrographolide: cellular response to MCF 7 breast cancer cells," BMC Cancer, 2004, vol. 4, No. 26.

Yuntao Duan, et al., "$Ca2+$ -dependent generation of mitochondrial reactive oxygen species serves as a signal for poly(ADP-ribose) polymerase-1 activation during glutamate excitotoxicity," J. Physiol., 2007, 741-758.

Mark G. Charest, et al., "A Convergent Enantioselective Route to Structurally Diverse 6-Deoxytetracycline Antibiotics," Science, Apr. 15, 2005, vol. 308, 395-398.

Yoori Choi, et al., "Minocycline Attenuates Neuronal Cell Death and Improves Cognitive Impairment in Alzheimer's Disease Models," Neuropsychopharmacology, 2007, vol. 32, 2393-2404.

Vincenzo Tumiatti, et al., "Progress in acetylcholinesterase inhibitors for Alzheimer's disease: an update," Expert Opin. Ther. Patents, 2008, vol. 18, No. 4, 387-401.

PCT/US09/50296 International Search Report and Written Opinion, dated Sep. 16, 2009.

Juha Yrjanheikki, et al., "Tetracyclines inhibit microglial activation and are neuroprotective in global brain ischemia," PNAS, Dec. 22, 1998, vol. 95, No. 26, 15769-15774.

Robert M. Sapolsky, "Glucocorticoids and Hippocampal Atrophy in Neuropsychiatric Disorders," Archives of General Psychiatry, Oct. 1, 200, vol. 57, No. 10, 925-935.

European Search Report, EP 09795257.6 (PCT/US2009050296), dated Jul. 13, 2012.

Official Action dated May 4, 2015, issued in corresponding Canadian Patent Application No. 2,730,377, filed Jul. 10, 2009, 4 pages.

TETRACYCLINE DERIVATIVES WITH REDUCED ANTIBIOTIC ACTIVITY AND NEUROPROTECTIVE BENEFITS

CROSS-REFERENCE TO RELATED APPLICATIONS

This application is a continuation of U.S. patent application Ser. No. 14/860,803, filed on Sep. 22, 2015, now issued as U.S. Pat. No. 9,573,912, which is a continuation of U.S. patent application Ser. No. 13/714,052, filed on Dec. 13, 2012, now issued as U.S. Pat. No. 9,168,265, which is a continuation of U.S. patent application Ser. No. 12/501,202, filed on Jul. 10, 2009, now issued as U.S. Pat. No. 8,338,477, which claims priority from U.S. Provisional Patent Application No. 61/080,114, filed on Jul. 11, 2008, which are hereby incorporated by reference in their entirety.

STATEMENT OF GOVERNMENTAL SUPPORT

This invention was not made with U.S. Government support.

REFERENCE TO SEQUENCE LISTING, COMPUTER PROGRAM, OR COMPACT DISK

None.

BACKGROUND OF THE INVENTION

Field of the Invention

The present invention relates to the field of compounds for the treatment and/or prevention of neurodegenerative diseases.

Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Cell Division and Alzheimer's Disease ("AD")

Reisberg US 2004/0127471, published Jul. 1, 2004, entitled "Methods of treating age associated memory impairment (AAMI), mild cognitive impairment (MCI), and dementias with cell cycle inhibitors," discloses a number of mechanisms which are attributed to neurodegenerative diseases. Among these are the suggestion that tetracycline-based compounds, in addition to inhibiting neuronal cell cycle progression at either an early cell cycle phase or generally, either alone or in combination with one or more agents are capable of reducing mitogenic stimulation and offering neuroprotection to patients with neurodegenerative diseases.

Reisberg further suggests that normal cell division occurs through a molecular biologic process known as the cell cycle. The cell cycle consists of major phases known as the G 1 phase, the S phase, the G 2 phase, the M phase and the G 0 phase. These phases of cell division correspond to the early growth phase, the synthesis phase, a later growth phase, a mitosis phase, and a resting phase. Progression through these phases is regulated by a series of enzymes, which include activators and inhibitors. However, this publication does not disclose that the compounds contemplated actually inhibit cell cycle progression.

Wang et al., "Minocycline inhibits caspase-independent and -dependent mitochondrial cell death pathways in models of Huntington's disease," *Proc. Nat. Acad. Sci.,* 100(18) 10483-10487 (2003), report that minocycline is a drug that directly inhibits both caspase-independent and -dependent mitochondrial cell death pathways.

Yang et al., "Ectopic Cell Cycle Events Link Human Alzheimer's Disease and Amyloid Precursor Protein Transgenic Mouse Models," *The Journal of Neuroscience,* Jan. 18, 2006, 26(3):775-784, disclose results which document the initiation of a cell-cycle process in the neurons of several mouse models of familial AD. There are a growing number of conditions in the mouse in which neuronal cell death is associated with re-entrance into a lethal cell cycle. The authors further state that several transgenic mouse models have been generated that recreate the genetic changes found in familial AD. Transgenic mice expressing mutant human amyloid precursor protein (APP) genes exhibit an age-related development of diffuse and neuritic plaques, with plaque burdens often approaching those found in advanced cases of AD. This has proven to be a valuable resource in the exploration and design of disease therapies. In addition, the AD mice show microglial activation, astrocytosis, and changes in neuronal cytoskeletal proteins including tau. Many of these model organisms have also been shown to have significant memory deficits. Despite these parallels to the human disease state, however, none of the mouse models has yet been shown to develop the typical neurofibrillary tangles. The reason for the discrepancy between the human and mouse neurodegenerative phenotype is unclear. However, there has been shown a close association between the neuronal cell death in AD and cellular processes that normally only occur during a mitotic cell cycle. Cell-cycle-related proteins are expressed in neurons that are "at risk" in AD but not in age-matched controls or in regions of the AD brain itself where degeneration is not prevalent. This ectopic re-expression of cell-cycle markers is functional as shown by fluorescent in situ hybridization (FISH).

Tetracycline Derivatives

A number of patents and publications disclose tetracycline derivatives and methods of their preparation, such as, U.S. Pat. No. 7,056,902, entitled "4-dedimethylamino tetracycline compounds", issued Jun. 6, 2006; U.S. Pat. No. 7,094, 806, entitled "7, 8 and 9-substituted tetracycline compounds," issued Aug. 22, 2006; U.S. Pat. No. 7,202,235, entitled "Tetracycline compounds for treatment of cryptosporidium parvum related disorders," issued Apr. 10, 2007; and U.S. Pat. No. 7,208,482, entitled "9-aminoacyl tetracycline compounds and methods of use thereof," issued Apr. 24, 2007. EP20020748169, by Levy, et al., published Apr. 1, 2004, entitled, "Tetracycline compounds having target therapeutic activities," discloses various synthetic routes to tetracycline derivatives. US 2007/0093455 to Abato et al., entitled "10-Substituted Tetracyclines and Methods of use thereof," published Apr. 26, 2007, purports to disclose compounds with 9-10 rings, e.g., at page 9. Exemplary compound Q showed superior inhibition of bacteria.

Use of Minocycline

US 20030092683 by Yansheng Du, et al., published May 15, 2003, entitled "Use of tetracyclines as neuro-protective agents and for the treatment of Parkinson's disease and related disorders," discloses the use of a tetracycline, preferably minocycline, for manufacture of a pharmaceutical composition for treatment or prevention of a disorder selected from Parkinson's disease and related disorders, such as Alzheimer's disease. The mechanism of action of the desired protection is not discussed, nor are minocycline alternatives.

This is in contrast to the present invention, described below, which, inter alia, does not use minocycline or other known tetracycline derivatives, and, further, uses compounds which do not have antibiotic activity.

BRIEF SUMMARY OF THE INVENTION

The following brief summary is not intended to include all features and aspects of the present invention, nor does it imply that the invention must include all features and aspects discussed in this summary.

Using the ring numbering of minocycline, compounds of the present invention may be represented as follows. In one embodiment, the compounds have the formula:

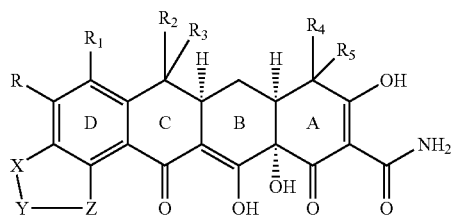

Formula I where each of X, Z, R, R1, R2, R3, R4 and R5 is selected from the group consisting of H, halogen, $C_{1-6}$ alkyl, $C_{1-6}$ haloalkyl, $C_{2-6}$ alkenyl, $C_{2-6}$ alkynyl, $C_{1-6}$ haloalkoxy, $NR^{1a}R^{1a}$, $OR^{1a}$, $SR^{1a}$, $-C(O)R^{1a}$, $-C(O)OR^{1a}$, $-C(O)NR^{1a}R^{1a}$, $-N(R^{1a})C(O)R^{1a}$, $-N(R^{1a})C(O)OR^{1a}$, $-N(R^{1a})C(O)NR^{1a}R^{1a}$, $-OP(O)(OR^{1a})2$, $-S(O)2OR^{1a}$, $-S(O)2NR^{1a}R^{1a}$, $-CN$, a 5-10 membered heterocycloalkyl ring structure having from 1-3 heteroatoms each of N, O or S, such that the heterocyccycloalkyl ring is substituted with 1-3 $R^{1a}$ groups, and a 5-10 membered heteroaryl ring structure having from 1-3 heteroatoms each of N, O or S, such that the heteroaryl ring is substituted with 1-3 $R^{1a}$ groups. $R^{1a}$ and $R^{2a}$ are H, or $C_{1-6}$ alkyl.

Further, in Formula I, Y is defined as either absent, and Z=OH or OCH3 and X=H, or XYZ taken together form a 5-10 membered heterocyloalkyl ring structure having from 1-3 heteroatoms each of N, O or S, or a 3-10 membered heteroaryl ring structure having from 1-3 heteroatoms each of N, O or S, such that the heterocycloalkyl or heteroaryl are substituted with 1-3 $R^{1a}$ groups, as illustrated in FIGS. 1 and 2.

In an alternative aspect of Formula I, R is combined with $R_1$ or X, and $R_1$ is combined with $R_2$ or $R_3$, along with the atoms to which each is attached, to form a 5-10 membered cycloalkyl, a 5-10 membered heterocyloalkyl ring structure having from 1-3 heteroatoms each of N, O or S, or a 5-10 membered heteroaryl ring structure having from 1-3 heteroatoms each of N, O or S, such that the cycloalkyl, heterocycloalkyl or heteroaryl is substituted with 1-3 $R^{2a}$ groups.

In an alternative aspect of Formula I, R2 is combined with R3, and R4 is combined with R5 to form a 5-10 membered cycloalkyl, or a 5-10 membered heterocyloalkyl ring structure having from 1-3 heteroatoms each of N, O or S.

In an alternative embodiment, the compounds have the formula:

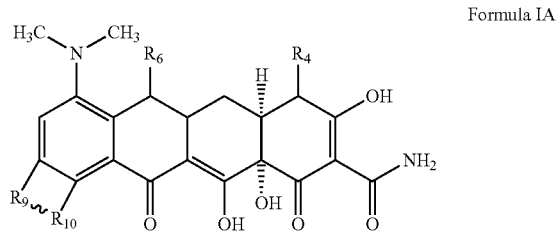

Formula IA $R_4$, $R_6$, $R_9$ and $R_{10}$ are described in detail below in the section entitled "Overview," and in connection with Table 1. Formula IA is a subset of Formula I. As is customary, hydrogen atoms are not shown explicitly, e.g., at R4 and R6 positions. The default values for the substituents in Formula IA (i.e., if they are not specified) are based on the structure of minocycline, namely as defined in Table I below. In yet another alternative embodiment, the compounds have Formula A

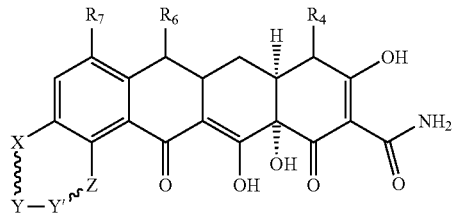

In Formula A, $R_4$, $R_6$, $R_7$, X, Y, Y' and Z are described as follows:

(a) R4, R6 and R7 are selected from the group consisting of H, $C_{1-10}$ alkyl, $C_{1-10}$ alkenyl, $C_{1-10}$ alkynyl, $C_{5-10}$ alkyl ring, $C_{5-10}$ aryl ring, $-C(=O)R^{1a}$, $-NR^{1a}R^{1a}$, $-SR^{1a}R^{1a}$, OH, and $OR^{1a}R^{1a}$;

(b) X, Y and Z are each individually selected from the group consisting of $-CR^{1a}R^{1a}-$, $-CR^{1a}(OH)-$, $-C(=O)-$, $-O-$, and $-NR^{1a}-$ and $-S-$;

(c) Y' is optionally present, and when Y' is present, Y and Y' taken together form a structure selected from the group consisting of $-C(R^{1a}R^{1a})C(R^{1a}R^{1a})-$, $-C(R^{1a}R^{1a})C(R^{1a}R^{1a})C(R^{1a}R^{1a})-$, $-C(=O)C(R^{1a}R^{1a})-$, $-C(R^{1a}R^{1a})O-$, $-C(R^{1a}R^{1a})N(R^{1a})-$, $-C(R^{1a}R^{1a})S-$, $-C(R^{1a}R^{1a})C(=O)C(R^{1a}R^{1a})-$, $-C(R^{1a}R^{1a})C(R^{1a}R^{1a})O-$, $-C(R^{1a}R^{1a})C(R^{1a}R^{1a})NR^{1a}-$, and $-C(R^{1a}R^{1a})C(R^{1a}R^{1a})S-$;

(d) bonds X—Y, Y—Y' and Y—Z may be single or double; and (e) $R^{1a}$ is independently selected from the group consisting of H, and $C_{1-10}$ alkyl.

Formula A is also a subset of Formula I. The compounds also include tautomers, salts, hydrates and prodrugs thereof.

In another embodiment, the compounds have the formula

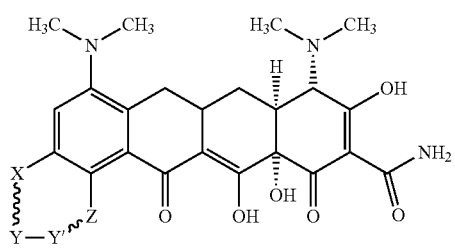

Formula A1

Formula A1 is a subset of Formula A and includes the below described compounds 3A, 3B and 38. $R_4$, $R_6$ and $R_7$ are in this case specified as dimethyl amino or hydrogen. X, Y, Y' and Z are described in detail below.

The compounds in the above formulas may also include tautomers, salts, hydrates and prodrugs thereof. As is conventional, the text formulas use parentheses to indicate groups pendant to an indicated chain or to indicate where a particular substituent is attached. For example, the X—Y—Y'—Z ring in the case of compound 3b is written —NH—C(=O)—O— for added clarity with regard to the carbonyl carbon at Y. In certain aspects, the present invention comprises compounds and compositions where, in Formula A, $R_4$ $R_6$ and $R_7$ are further selected from the group consisting of H, OH, and $C_{1-10}$ alkyl, which alkyl is substituted with 0-3 amine or hydroxyl groups. In certain aspects, the present invention comprises compounds and compositions where, in Formula A, or subsets of Formula A, X is amino, Y is C=O, and Z is O. In certain aspects, the present invention comprises compounds and compositions where, in Formula A, or subsets of Formula A, $R_6$ is further selected from the group consisting of H and $C_{1-10}$ alkyl. In certain aspects, the present invention comprises compounds and compositions where, in Formula A, where —X~Y—Y'~Z— is defined by a formula selected from the group consisting of —N=CH—O—, —NH—C(=O)—O—, and —NH—C(=O)—CH$_2$—O—. In certain aspects, the present invention comprises compounds and compositions where, in Formula A, or subsets of Formula A, where $R_7$ is —NR$^{1a}$R$^{1a}$ and/or wherein $R_4$ is —NR$^{1a}$R$^{1a}$. In certain aspects, the present invention comprises compounds and compositions where, in Formula A, or subsets of Formula A, a particular stereoisomer is isolated, such as an epimer at $R_4$, which may be represented as an up epimer. In certain aspects, the present invention comprises compounds and compositions where, in Formula A, or subsets of Formula A, $R_6$ is H, OH, or $C_{1-10}$ alkyl. In certain aspects, the present invention comprises compounds and compositions where, in Formula A, or subsets of Formula A, $R_7$ is —N—(CH$_3$)$_2$. In certain aspects, the present invention comprises compounds and compositions where, in Formula A, or subsets of Formula A, X is —N=, Y is —CH—, and Z is —O—. In certain aspects, the present invention comprises compounds and compositions where, in Formula A, or subsets of Formula A, X is —NH—, Y is —C(=O)— and Z is —O—. In certain aspects, the present invention comprises compounds and compositions where, in Formula A, or subsets of Formula A, X is —NH—, Y—Y' is —C(=O)—CH$_2$— and Z is —O—. In certain aspects, the present invention comprises compounds and compositions where, in Formula A, or subsets of Formula A, wherein R4 and R7 are —N(CH$_3$)$_2$— and $R_6$ is H. In certain aspects, the present invention comprises a method of treating and/or ameliorating a neurodegenerative disease, comprising the step of administering to a subject in need thereof a composition comprising a therapeutically effective amount of a compound according to Formula A, or its various subsets. The neurodegenerative disease may be one of a variety of neurodegenerative diseases, and may in certain aspects, be a disease of the brain, such as Alzheimer's Disease.

Other aspects of the present invention involve treatment of preventing age associated memory impairment (AAMI), subjective cognitive impairment, (SCI), mild cognitive impairment (MCI), Alzheimer's disease (AD), cerebrovascular dementia (CVD) and related degenerative neurological conditions. This treatment may be accompanied by administration of other agents. According to the present inventive methods, these may include one or more secondary agents selected from the group consisting of acetylsalicylic acid, any salicylate which inhibits early phase cell cycle progression, sirolimus, any sirolimus derivative capable of inhibiting early cell cycle progression, flavopiridol, ciclopirox, a paulone, indirubin, fascaplycin, olomoucine, roscovitine, Aragusterol A, valproate, N-(3-chloro-7-indolyl)-1,4-benzenedisulfamide, a farnesyl transferase inhibitor such as R115777, SCH66336 and BMS-214662, and sodium butyrate. Treatment (as defined herein) will be with a therapeutically effective amount. In another aspect, the present invention comprises a method of identifying a neuroprotective compound, comprising the steps of synthesizing a tetracycline compound according to according to Formula A. In certain aspects, the present invention comprises compounds and compositions where, in Formula A, or subsets of Formula A, according to the formula

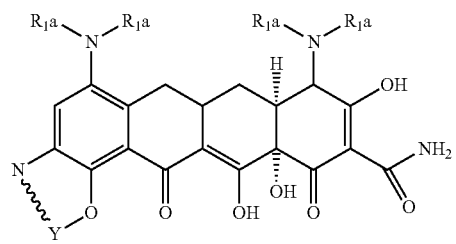

where Y is selected from the group consisting of lower alkylene and lower heteroalyklene; R$_1$a is independently selected from the group consisting of H and C$_{1-6}$ alkyl; and the bond between N and Y may be single or double; and salts and esters thereof. In addition, in the above formula, in certain aspects, X may be selected from the group consisting of lower alkylene and lower heteroalyklene, R$_1$a is independently selected from the group consisting of H, C$_{1-10}$ alkyl, branched C$_{1-10}$ alkyl, and branched C$_{1-10}$ alkyl; and the bond between N and X may be single or double. In certain aspects of the present invention, the compounds are in a pharmaceutically acceptable excipient. They may be in an oral formulation.

In one embodiment, the invention pertains to a method for treating a disease with a tetracycline compound having a target therapeutic activity, which includes activities of tetracycline compounds in a subject that differ from antibacterial and/or anti-infective activity or are in addition to antibacterial and/or anti-infective activity, but result in treatment of a certain disease. This is based on the idea that, by both the expression of cell-cycle proteins and the documentation of DNA replication, normally postmitotic cells attempt a process that strongly resembles a mitotic cell division in certain disease states, such as in mouse models of AD.

In certain aspects, the present invention comprises a neuroprotective composition comprising a therapeutically effective amount of a tetracycline-type compound that is substantially not antibiotic and is inhibitory of cell cycle progression in a neuronal cell. The tetracycline compound may be a minocycline derivative. The present compounds may take on a variety of structures, and are based on modifications of known compounds, as described below. The compound may be regarded as a minocycline derivative, or any minocycline family derivative in that, like minocycline, it has favorable capacity to cross the blood brain barrier.

Some exemplary compounds according to the present invention are as follows:

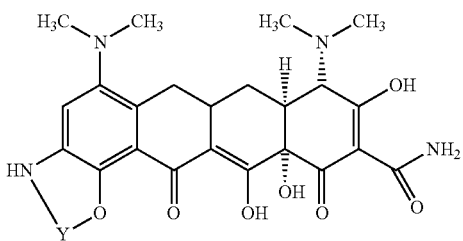

Compound 3—Y=CH and the N—Y bond is a double bond; or Y=C=O; or Y=C(=O)—CH$_2$—.

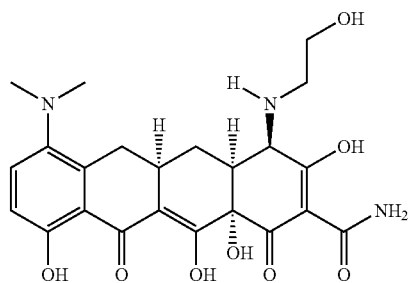

Compound 12—R$_4$=NH—CH$_2$CH$_2$CH$_2$—OH, up bond at minocycline position

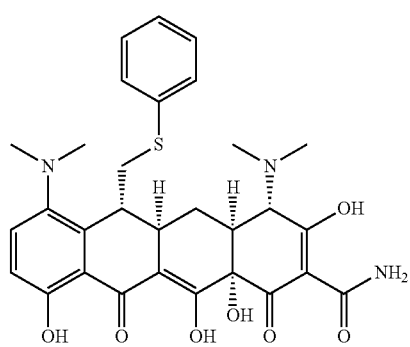

Compound 14—R$_6$=CH2-S-aryl (phenyl), down bond at position 4.

In another aspect, the present invention provides a pharmaceutical composition including a pharmaceutically acceptable carrier and a compound of the present invention.

In a further aspect, the present invention further comprises a method of ameliorating (i.e., treating, preventing or stabilizing) a neurodegenerative disease in a subject who has been identified as having or at significant risk for said neurodegenerative disease (e.g., Alzheimer's Disease, Lewy bodies, etc.) The method comprises administering to the subject in need thereof a composition comprising a therapeutically effective dose of a compound as referred to above. In one aspect of the present invention, the compound is capable of inhibiting neuronal cell cycle progression before entry of a neuronal cell into a synthesis (S) phase, or the early growth (G1) phase. Progression of later phases is not preferred, because the active cell machinery involved in mitosis is implicated in the neuronal death sought here to be prevented. However, the present invention also contemplates certain combination therapies, which may include combinations of the present compounds as well as compounds involved in later phases of the cell cycle. In particular, the present compounds are useful in treating or preventing age associated memory impairment (AAMI), subjective cognitive impairment (SCI), mild cognitive impairment (MCI), Alzheimer's disease (AD), cerebrovascular dementia (CVD) and related degenerative neurological conditions.

In certain aspects, the present invention comprises methods for identifying neuroprotective compounds. These compounds, in particular, will prevent the death or loss of function of neurons of the central nervous system, especially in the brain. The method comprises the steps of:
(a) synthesizing a tetracycline compound;
(b) testing said compound for antibiotic activity;
(c) testing said compound for cell cycle inhibition (mainly by testing for inhibition of the poly(ADP-ribose) polymerase (PARP) enzyme, as described below); and
(d) if said compound shows substantially no antibiotic activity and shows cell cycle inhibitory activity, testing such compound in an animal model of neuronal damage.

In certain aspects, the present invention includes compounds which are tetracycline derivatives which are substantially not antibiotic, and, also have significant inhibitory activity against poly(ADP-ribose) polymerase as a measure of inducing apoptosis, and, further, cross the blood brain barrier in sufficient degree to affect cells of the brain and surrounding tissue. The above method may consist essentially of the above steps or the steps of testing for antibiotic activity, PARP inhibition and blood brain barrier permeability.

DETAILED DESCRIPTION OF THE PREFERRED EMBODIMENT

Definitions

Figure 1:
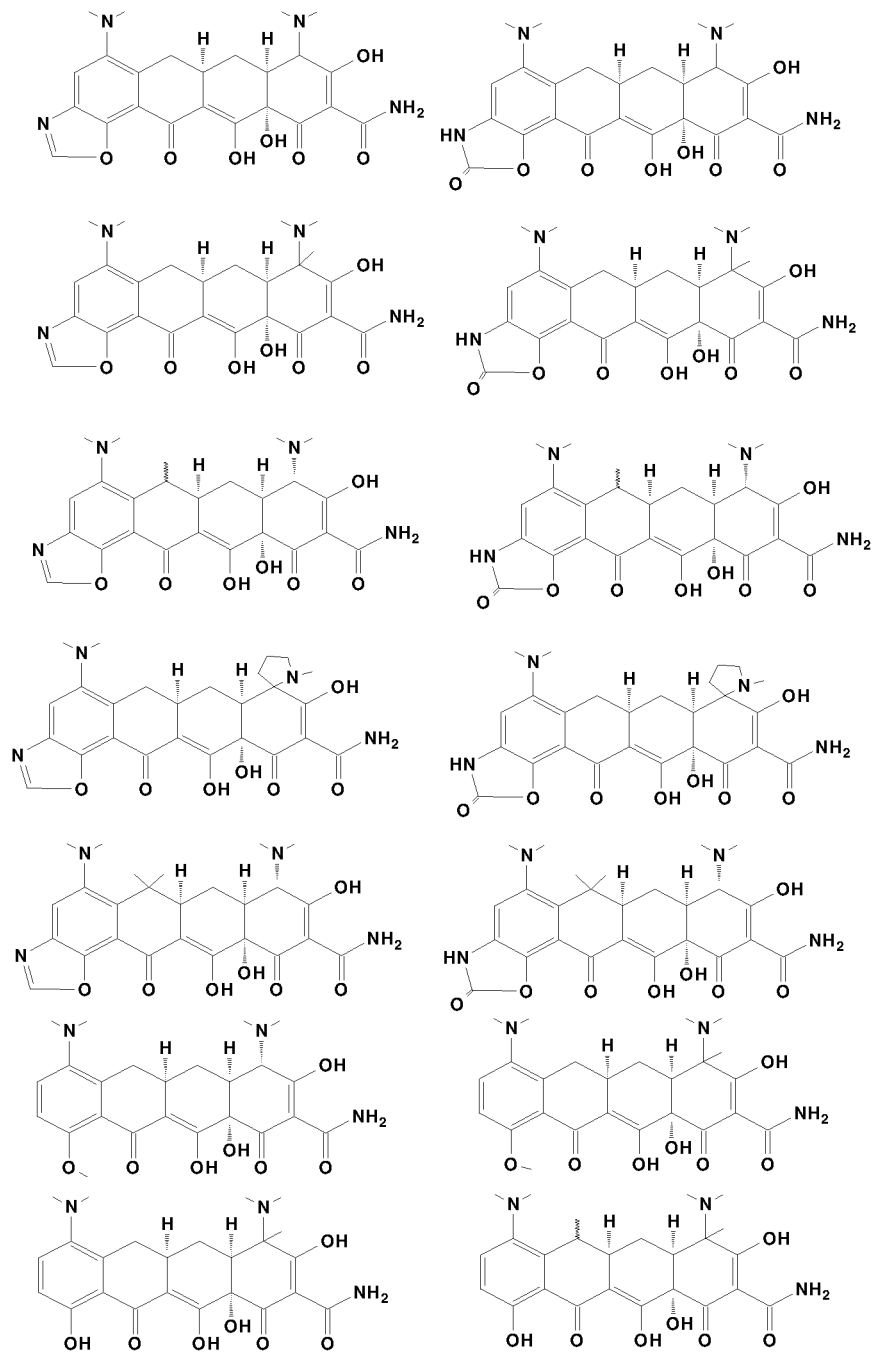
FIG. 1 shows examples of compounds according to the present invention.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "antibiotic activity" means, in reference to the compounds of the present invention, that the compounds have a minimal effect on the growth of bacteria normally sensitive to minocycline antibiotics. As described in Connell et al., "Ribosomal Protection Proteins and Their Mechanism of Tetracycline Resistance," *Antimicrobial Agents and Chemotherapy*, December 2003, p. 3675-3681, Vol. 47, No. 12, tetracyclines can be separated into two groups, the atypical tetracyclines (e.g., anhydrotetracycline and 6-thiatetracycline) and typical tetracyclines (e.g., tetracycline, chlortetracycline, and minocycline). The atypical tetracyclines function by disrupting bacterial membranes. Alternatively, the typical tetracyclines, which are the subject of Ribosomal Protection Proteins (RPP)-mediated resistance, bind to the ribosome and inhibit the elongation phase of protein synthesis. More precisely, they inhibit accommodation of aminoacyl-tRNA (aa-tRNA) into the ribosomal A site and, therefore, prevent the addition of new amino acids to the growing polypeptide. The present compounds, lacking antibiotic activity, will have minimal of such activity, i.e., minimal binding to bacterial ribosomes, and will have less than 50%, preferably less than 10% of the antibacterial activity of a related tetracycline antibiotic, as measured in a standard MIC assay. For explanation of the term MIC measurements, see, e.g., U.S. Pat. No. 6,140,069. Thus, the phrase "substantially not antibiotic" means a compound having little or no antibiotic activity as measured in standard antibiotic sensitivity tests using cultured microorganisms such as *E. coli S. aureus*, etc. Examples are given below.

The term "tetracycline derivative" includes substituted tetracycline compounds or compounds with a similar ring structure to tetracycline. Other derivatives and analogues comprising a similar four-ring structure are also included (See Rogalski, (1984) "Chemical Modification of the Tetracyclines," In: The tetracyclines. Hlavka J J, Boothe J H, editors. New York: Springer-Verlag Press, pp. 179-309, the entire contents of which are hereby incorporated herein by reference). In particular, one may begin with a structure as shown as compound 2 in Scheme 1, or with minocycline.

The term "neuroprotective" means a treatment that has an effect that reduces, arrests, or ameliorates nervous insult and is protective, resuscitative or revivative for nervous tissue that has suffered nervous insult, particularly in the case of a suspected neurodegenerative disease. It may include reduction of neuronal death or loss of function in diseases such as AD, age associated memory impairment, mild cognitive impairment, cerebrovascular dementia, etc. The present term is associated with neurodegenerative diseases, which may be diagnosed by known methods, including biomarkers, PET imaging, etc. For examples of determining the existence and progression of these neurodegenerative diseases, see: Mueller et al., "Evaluation of treatment effects in Alzheimer's and other neurodegenerative diseases by MRI and MRS," *NMR Biomed*, 2006 October; 19(6): 655-668. As described there, Neurodegeneration refers to a large clinically and pathologically heterogeneous disease entity associated with slowly progressive neuronal loss in different anatomical and functional systems of the brain. Neurodegenerative diseases often affect cognition, e.g., Alzheimer's disease (AD), dementia with Lewy bodies and vascular dementia, or different aspects of the motor system, e.g., amyotrophic lateral sclerosis, Parkinson's disease and ataxic disorders. In particular, the present compounds and methods are preferred for use in protection of neurons in the brain, inasmuch as they pass the blood brain barrier.

The term "cell cycle progression" as used herein means the progression of a cell through the cell cycle described above, and, preferably, from G0 to G1 or from G1 to S. A compound which is inhibitory of cell cycle progression may be determined by known assays. Identification of compounds which produce a G1 block is described in Toogood et al., "Cyclindependent kinase inhibitors for treating cancer," *Med Res Rev.*, 2001 November; 21(6):487-98.

The term "alkyl", by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e., $C_1$-$C_{10}$ means one to ten carbons). Preferably an alkyl chain contains from 1 to 40 carbon atoms, more preferably 1 to 10 carbon atoms, and even more preferably 1 to 6 carbon atoms. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl) methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-butadienyl), 2,4-entadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic ("heterocyclic alkyl"), heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_3$H, guanido, and —SO$_2$-heteroaryl.

The term "alkylene", by itself or as part of another substituent, means a divalent radical derived from an alkyl group as defined above, as exemplified, but not limited, by —CH$_2$CH$_2$CH$_2$CH$_2$—, and further includes those groups described below as "heteroalkylene." Typically, an alkylene group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms, preferably six or fewer carbon atoms, more preferably three or fewer carbon atoms. Examples of alkylene groups are —C(=O)—, —CH$_2$—C(=O)—, —CH$_2$—CH$_2$—, —CH$_2$=CH—, —C(SH$_2$)—, —CH2-C(NH$_2$)—, etc. In the case of lower heteroalkyl or heteroalkylene, there will be 1-2 heteroatoms counted as part of the group.

As used herein, the term "alkenyl" refers to either a straight chain or branched hydrocarbon of 2 to 10, preferably 2-6 carbon atoms, having at least one double bond. Examples of alkenyl groups include, but are not limited to, vinyl, propenyl, isopropenyl, butenyl, isobutenyl, butadienyl, pentenyl or hexadienyl. These groups may be substituted as described in connection with alkyl groups.

As used herein, the term "alkynyl" refers to either a straight chain or branched hydrocarbon of 2 to 10, preferably 2 to 6 carbon atoms, having at least one triple bond. Examples of alkynyl groups include, but are not limited to, acetylenyl, propynyl or butynyl. These groups may be substituted as described in connection with alkyl groups.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "acyl" refers to a moiety that is a residue of a carboxylic acid from which an oxygen atom is removed, i.e., —C(=O)R, in which R is substituted or unsubstituted alkyl, substituted or unsubstituted heteroalkyl, substituted or unsubstituted heterocycloalkyl, substituted or unsubstituted aryl or substituted or unsubstituted heteroaryl.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene" by itself or as part of another substituent means a divalent radical derived from heteroalkyl, as defined and exemplified above, but not limited by, —CH$_2$—CH$_2$—S—CH$_2$—CH2- and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2 piperazinyl, and the like.

The term "heterocyclic alkyl" means an alkyl group as defined above, which contains a heteroatom (heteroalkyl) and is joined to the scaffold (i.e., fused ring structure) at 2 positions to form a fused ring. Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO$_2$-alkyl, —SO$_2$-substituted alkyl, —SO$_2$-aryl, oxo (=O), and —SO$_2$-heteroaryl. Such heterocyclic groups can have a single ring or multiple condensed rings. Preferred heterocyclics include morpholino, piperidinyl, and the like.

The term "aryl" means, unless otherwise stated, a polyunsaturated, typically aromatic, hydrocarbon substituent, which can be a single ring or multiple rings (up to three rings) which are fused together, linked covalently, or linked to a common group such as a methylene or ethylene moiety. The common linking group may also be a carbonyl as in benzophenone. The aromatic ring(s) may include substituted or unsubstituted phenyl, naphthyl, biphenyl, diphenylmethyl and benzophenone among others. In particular embodiments, aryls have between 1 and 200 carbon atoms, between 1 and 50 carbon atoms or between 1 and 20 carbon atoms.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "substituted aryl" refers to aryl as just described including one or more functional groups such as lower alkyl, acyl, halogen, alkylhalos (e.g., $CF_3$), hydroxy, amino, cyano, phosphido, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like. Other terms such as "haloalkoxy" refer to halogen substituted alkoxy groups.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO2R', —CONR'R", —OC(O)NR'R", —NR"C(O)R', —NR'—C(O)NR"R'", —NR"C(O)2R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)2R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X(CR"R'")d-, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

The term "moiety" refers to the radical of a molecule that is attached to another moiety.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

The symbol ⌇, whether utilized as a bond or displayed perpendicular to a bond indicates the point at which the displayed moiety is attached to the remainder of the molecule, solid support, etc. The present structures include epimers, which are indicated conventionally and refer to a single stereoisomer.

The term "pharmaceutically acceptable salts" includes salts of the active compounds prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, palmitic and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

A "pharmaceutically acceptable" excipient is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

In some embodiments "therapeutically effective amount" refers to a safe and effective amount of a component effective to yield the desired therapeutic response, for example, an amount effective to prevent or treat (ameliorate) neurodegeneration, memory loss, or dementia.

The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

An "oral formulation" is a formulation of a compound wherein the compound is formulated for ingestion by mouth.

As used herein, the terms "treat," refers to any indicia of success in the treatment or amelioration of an injury, pathology, condition, or symptom (e.g., cognitive function), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The amelioration of symptoms can be based on any objective or subjective parameter; including, e.g., the result of a physical examination.

Overview

The present invention relates to methods and compositions for therapeutic treatments or prevention of age associated memory impairment (AAMI), subjective cognitive impairment (SCI), mild cognitive impairment (MCI), Alzheimer's disease (AD), cerebrovascular dementia (CVD), and related neurodegenerative conditions by administering a chemically modified tetracycline core compound, e.g., a minocycline based compound, that exhibits a combination of (a) blood-brain barrier penetration, (b) low antibiotic activity and (c) is capable of inhibiting cell cycle progression, particularly neuronal cell cycle progression. All of these compounds when administered either as an oral dose, prodrug, injection or inhalable solution or powdered matrix or in combination with one or more agents are capable of inhibiting neuronal cell cycle progression at either an early cell cycle phase or generally, either alone or in combination with one or more agents capable of reducing mitogenic stimulation.

As described above, a suggestion has been found in the art to use minocycline for neurodegenerative diseases. However, the present invention involves the recognition that dosing patients with antibiotic compounds will confer unwanted antibiotic activity that may cause or create harm to a patient because of either short term or prolonged therapeutic administration. Minocycline 9-hydroxylation and N-demethylation has been reported in humans, but only to a limited extent (H J Nelis, A P De Leenheer—Drug Metabolism and Disposition, 1982—ncbi.nlm.nih.gov). Epimerization at the C4 position has also been reported for most tetracycline antibiotics and is generally considered as degradation product rather than a metabolic pathway. (E G Remmers, G M Sieger, A P Doerschuk—*Journal of Pharmaceutical Science*, 1963—*J Pharm Sci.* 1963 August; 52:752-6. Some Observations On The Kinetics Of The C.4

The invention utilizes a chemically modified tetracycline scaffold, preferably the scaffold of minocycline, and neutralizes or significantly inhibits antibiotic activity, while preserving or enhancing neuroprotective attributes without interfering with the drugs' capacity to pass through the blood brain barrier.

Chemically Modified Tetracycline Core Compounds Lacking Antibiotic Activity

The present compounds have much less antibiotic activity than minocycline, i.e., essentially no antibiotic activity. However, they retain neuroprotective activity because of the diversity in structures, and have similar physical-chemical properties to minocycline in order to retain the ability to cross the blood brain barrier.

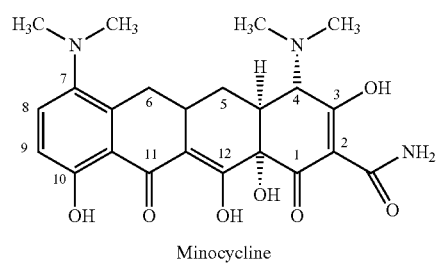

Minocycline

Using the ring numbering of minocycline, in one embodiment, compounds of the present invention may be represented as follows:

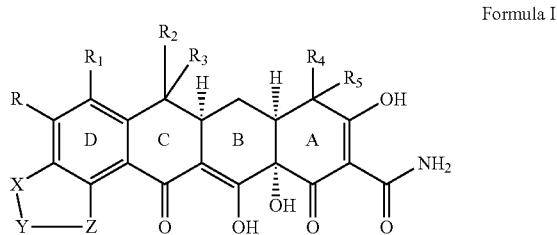

Formula I where each of X, Z, R, $R_1$, $R_2$, $R_3$, $R_4$ and $R_5$ is selected from the group consisting of H, halogen, $C_{1-6}$alkyl, $C_{1-6}$haloalkyl, $C_{2-6}$ alkenyl, $C_{2-6}$ alkynyl, $C_{1-6}$ haloalkoxy, $NR^{1a}R^{1a}$, $OR^{1a}$, $SR^{1a}$, $-C(O)R^{1a}$, $-C(O)OR^{1a}$, $-C(O)NR^{1a}R^{1a}$, $-N(R^{1a})C(O)R^{1a}$, $-N(R^{1a})C(O)OR^{1a}$, $-N(R^{1a})C(O)NR^{1a}R^{1a}$, $-OP(O)(OR^{1a})_2$, $-S(O)_2OR^{1a}$, $-S(O)_2NR^{1a}R^{1a}$, $-CN$, a 5-10 membered heterocycloalkyl ring structure having from 1-3 heteroatoms each of N, O or S, such that the heterocycloalkyl ring is substituted with 1-3 $R^{1a}$ groups, and a 5-10 membered heteroaryl ring structure having from 1-3 heteroatoms each of N, O or S, such that the heteroaryl ring is substituted with 1-3 $R^{1a}$ groups.

Where Y may be absent, and Z=OH or $OCH_3$ and X=H; or, alternatively, XYZ taken together form a 5-10 membered heterocycloalkyl ring structure having from 1-3 heteroatoms each of N, O or S, or a 5-10 membered heteroaryl ring structure having from 1-3 heteroatoms each of N, O or S, such that the heterocycloalkyl or heteroaryl are substituted with 1-3 $R^{1a}$ groups. $R^{1a}$ and $R^{2a}$ are H, or $C_{1-6}$ alkyl.

In an alternative aspect of Formula I, R is combined with $R_1$ or X, and $R_1$ is combined with $R_2$ or $R_3$, along with the atoms to which each is attached, to form a member a 5-10 membered cycloalkyl, a 5-10 membered heterocyloalkyl ring structure having from 1-3 heteroatoms each of N, O or S, or a 5-10 membered heteroaryl ring structure having from 1-3 heteroatoms each of N, O or S, such that the cycloalkyl, heterocycloalkyl or heteroaryl is substituted with 1-3 $R^{2a}$ groups.

In yet another alternative aspect of Formula I, $R_2$ is combined with $R_3$, and $R_4$ is combined with $R_5$ to form a member a 5-10 membered cycloalkyl, a 5-10 membered heterocyloalkyl ring structure having from 1-3 heteroatoms each of N, O or S.

In addition, the present Formula I (and Formula A) includes tautomers, salts, hydrates and prodrugs thereof of the above compounds.

Representative compounds from this embodiment, and the embodiment of Formula A, are shown in FIG. 1.

In another embodiment, compounds of the present invention may be represented as follows:

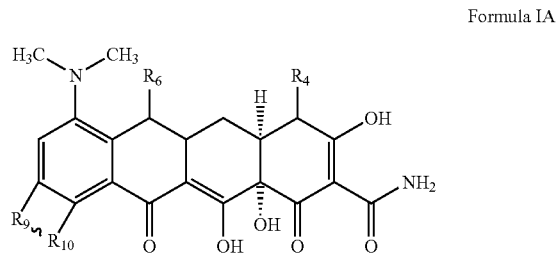

Formula IA

In this embodiment, essentially a subset of Formula I, the present compounds involve substituents at least one of $R_4$, $R_6$, $R_9$, or $R_{10}$ as shown in Formula IA. As is conventional the ring containing $R_9$ and $R_{10}$ is referred to as the D ring; $R_6$ is in the C ring; and $R_4$ is in the A ring. As described below, the most preferred route to obtaining the subject compounds involves modification of the D ring.

An important aspect of Formula A and Formula A1 is that they contain a ring between position 9 (which is unsubstituted in minocycline) and position 10 (which is hydroxy substituted in minocycline). This ring has been found to confer a lack of antibiotic activity and neuroprotective activity. This ring may be a 5 to 7 membered ring (counting carbons 9 and 10) and may contain 1 or two heteroatoms in place of carbon. The heteroatoms may be O, S or N. In addition, the carbons forming the additional ring may be substituted with O, S or N atoms.

These substituents are described in detail below in Table 1. The default values for the substituents in Formula IA (i.e., if they are not specified) are shown as "Default Group." Thus, if Formula IA is defined according to Table 1, preferably no more than one R substituent ('alternate' group(s)) will be present; the remainder of the R groups will be the "default" groups. In certain embodiments, two alternate groups, e.g., $R_4$ and $R_9$-$R_{10}$, or $R_4$ and $R_6$, or $R_{10}$ and $R_4$ are included.

TABLE 1

| R substituent | Default group | Alternate group(s) |
|---|---|---|
| $R_4$ | $N(CH_3)_2$; | "up" bonded $NH(CH_3)_2OH$; amino alkanols; disubstitution, R', $-N(CH_3)_2$, where R is substituted alkyl; disubstitution with amino alkyl and with lower alkyl. |
| $R_6$ | H; | $-S-R''$, where R" is aryl or substituted aryl, preferably benzyl or phenyl. |
| $R_9$ | H; | R9 and R10 taken together form a 5-10 membered alkyl or |
| $R_{10}$ | OH; | heteroalkyl ring; preferably of the formula (from R10 to R9) $-O-Y-HN-$, where Y is either CH, in which case the bond Y—N is double, or else C=O. Alternatively, R10 may be a lower substituted alkyl, and R9 is H. |

Epimeric Derivatives (R4)

Epimeric derivatives provide a number of preferred compounds. Epimerization of the 4-dimethylamino group ($R_4$) is known to eliminate antibiotic activity of the minocycline family. The present epimers also will affect cell cycling activity. The present epimers involve bonds at the 4 position, i.e., $R_4$, which is "down" in minocycline but "up" in the epimer. Compound 11 is the epimer of minocycline. In this connection, it is noted that the present compounds may be prepared in compositions which are optically pure, rather than racemic. Compounds prepared according to the synthetic methods disclosed here can be separated into single diastereoisomers or optically pure compounds by known chromatographic methods.

Compound 12 is a secondary amine derivative that is reported to be much slower to revert to the natural stereochemistry. Quaternization of position 4 as in compound 13 should reduce antibiotic activity as well. Both stereoisomers will be of interest. As illustrated below, Compound 11 is (4S,4aS,5aR,12aS)-4,7-bis(dimethylamino)-3,10,12,12a-tetrahydroxy-1,11dioxo-1,4,4a,5,5a,6,11,12a-octahydrotetracene-2-carboxamide; Compound 12 is (4S,4aS,5aR,12aS)-7-(dimethylamino)-3,10,12,12a-tetrahydroxy-4-(2-hydroxyethylamino)1,11-dioxo-1,4,4a,5,5a,6,11,12a-octahydrotetracene-2-carboxamide; and Compound 13, containing a lower alkyl or substituted alkyl R group is named, if R═CH$_3$, (4aS,5aR,12aS)-4,7bis(dimethylamino)-3,10,12,12a-tetrahydroxy-4-methyl-1,11-dioxo-1,4,4a,5,5a,6,11,12aoctahydrotetracene-2-carboxamide.

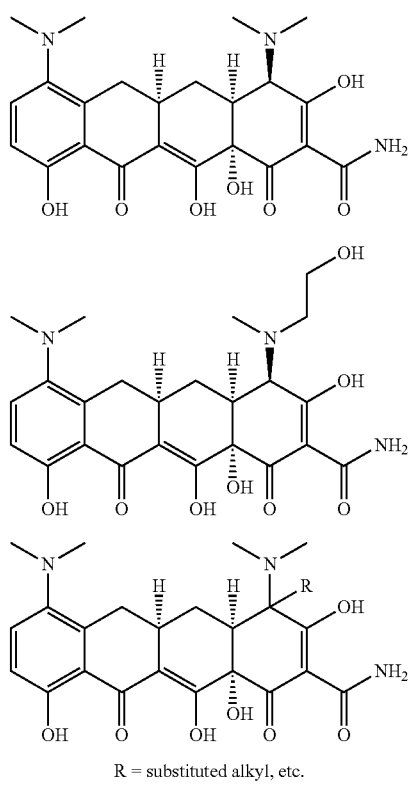

R = substituted alkyl, etc.

$R_6$ Derivatives

Subtle changes in the substituents at position 6 are introduced to reduce antibiotic potency of the present tetracycline compounds. In particular, sulfur derivatives of general structure 14 are expected to lack antibiotic activity. Compounds of structure 14 will be named as follows: If R═H, (4S,4aS,5aR,6R,12aS)-4,7-bis(dimethylamino)-3,10,12,12a-tetrahydroxy-6(mercaptomethyl)-1,11-dioxo-1,4,4a,5,5a,6,11,12a-octahydrotetracene-2-carboxamide; If R═Ph, (4S,4aS,5aR,6R,12aS)-6-(cyclohexylthiomethyl)-4,7-bis(dimethylamino)-3,10,12,12atetrahydroxy-1,11-dioxo-1,4,4a,5,5a,6,11,12a-octahydrotetracene-2-carboxamide; if R═Bn, 4S,4aS,5aR,6R,12aS)-4,7-bis(dimethylamino)-3,10,12,12a-tetrahydroxy-1,11-dioxo-6(phenylthiomethyl)-1,4,4a,5,5a,6,11,12a-octahydrotetracene-2-carboxamide.

$R_9$-$R_{10}$ Substituted Compounds

Simple chemistry transforms minocycline to its 9-nitro derivative, which is expected to have poor antibiotic activity. Reduction can take this to the 9-amino analog, which is known to be a good antibiotic. Further modification leading to cyclic derivatives, such as Compound 3, should abolish antibiotic activity by capping the critical phenolic OH at position 10.

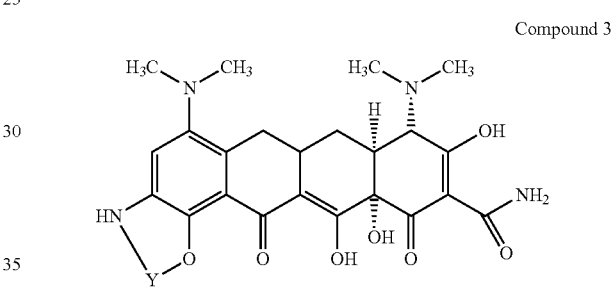

Compound 3

Compound 3 is named (6aR,7aS,8S,11aS)-5,8-bis(dimethylamino)-9,11a,12trihydroxy-11,13-dioxo-6,6a,7,7a,8,11,11a,13-octahydrotetraceno[2,1-d]oxazole-10carboxamide, when Y═—CH— (termed below compound 3a); and (6aR,7aS,8S,11aS)-5,8bis(dimethylamino)-9,11a,12-trihydroxy-2,11,13-trioxo-2,3,6,6a,7,7a,8,11,11a,13decahydrotetraceno[2,1-d]oxazole-10-carboxamide, when Y═—C(═O)— (termed below compound 3b). In addition, when Y═—C(═O)—C— (termed below compound 38), the compound is termed (6aR,7aS,8S,11aS)-5,8-bis(dimethylamino)-9,11a,12-trihydroxy-2,11,13trioxo-2,3,6,6a,7,7a,8,11,11a,13-decahydrotetraceno[2,1-d]morpholine-10-carboxamide.

Compound 3 may be further represented by Formula A:

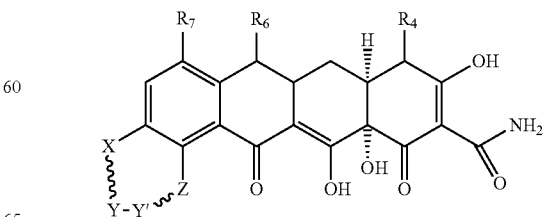

A more specific embodiment of Formula A is Formula 3B:

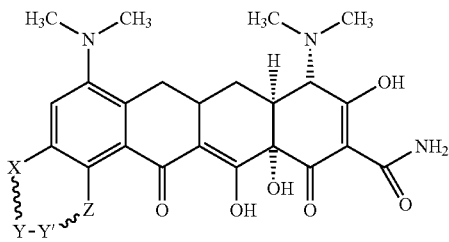

With regard to both of the above formulas,
(a) R4, R6 and R7 are selected from the group consisting of H, $C_{1-10}$ alkyl, $C_{1-10}$ alkenyl, $C_{1-10}$ alkynyl, $C_{5-10}$ alkyl ring, $C_{5-10}$ aryl ring, —C(=O)$R^{1a}$, —N$R^{1a}R^{1a}$, —S$R^{1a}R^{1a}$, OH, and O$R^{1a}R^{1a}$;
(b) X, Y and Z are each individually selected from the group consisting of —C$R^{1a}R^{1a}$—, —C$R^{1a}$(OH)—, —C(=O)—, —O—, and —N$R^{1a}$— and —S—;
(c) Y' is optionally present, and when Y' is present, Y and Y' taken together form a structure selected from the group consisting of —C($R^{1a}R^{1a}$)C($R^{1a}R^{1a}$)—, —C($R^{1a}R^{1a}$)C($R^{1a}R^{1a}$)C($R^{1a}R^{1a}$)—, —C(=O)C($R^{1a}R^{1a}$)—, —C($R^{1a}R^{1a}$)O—, —C($R^{1a}R^{1a}$)N($R^{1a}$)—, —C($R^{1a}R^{1a}$)S—, —C($R^{1a}R^{1a}$)C(=O)C($R^{1a}R^{1a}$)—, —C($R^{1a}R^{1a}$)C($R^{1a}R^{1a}$)O—, —C($R^{1a}R^{1a}$)C($R^{1a}R^{1a}$)N$R^{1a}$—, and —C($R^{1a}R^{1a}$)C($R^{1a}R^{1a}$)S—;
(d) bonds X—Y, Y—Y' and Y—Z may be single or double; and
(e) $R^{1a}$ is independently selected from the group consisting of H, and $C_{1-10}$ alkyl.

A variety of compounds and analogues comprising a similar four-ring structure may also be prepared according to the present teachings. For a review, see W. Rogalski, "Chemical Modifications of Tetracyclines," the entire contents of which are hereby incorporated herein by reference). Other modifications that can and cannot be made to the basic tetracycline structure have been reviewed by Mitscher in The Chemistry of Tetracyclines, Chapter 6, Miarcel Dekker, Publishers, New York (1978). According to Mitscher, the substituents at positions 5-9 of the tetracycline ring system may be modified without the complete loss of antibiotic properties. Changes to the basic ring system or replacement of the substituents at positions 1-4 and 10-12, however, generally lead to synthetic tetracyclines with substantially less or effectively no antimicrobial activity. An example is 4-dedimethylaminotetracyline which is commonly considered to be a non-antimicrobial tetracycline (See U.S. Pat. No. 6,914,057 for further details.)

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Syntheses

General synthetic strategies are outlined below. Other synthetic strategies may be used, starting with more simple compounds. For example, Charest et al., "A convergent Enantioselective Route to Structurally Diverse 6-Deoxytetracycline Antibiotics," Science 308:395398 (2005) describes methods using various D-ring precursors. This work is also described in US 2005/0282787. This method provides for the modular synthesis of tetracyclines and its various analogs by joining a highly functionalized chiral enone, which will become the A and B-rings of the tetracycline core, with a molecule that will become the D-ring of the tetracycline core. The joining of these two intermediates results in the formation of the C-ring, preferably in an enantioselective manner. This methodology also allows for the incorporation of heterocycles into the ring system. In particular, the joining of these two fragments includes various nucleophilic addition reactions and cycloaddition reactions with enone. It is noted that the compounds described there have significant antibiotic activity and must be modified according to the present teachings to lack antibiotic activity.

In addition, U.S. Pat. No. 5,834,450, issued to Su on Nov. 10, 1998, entitled "9(substituted amino)-alpha-6-deoxy-5-oxy tetracycline derivatives, their preparation and their use as antibiotics," discloses methods, which may be adapted according to the present teachings, for synthesizing 9-substituted tetracycline antibiotics.

Scheme 1.

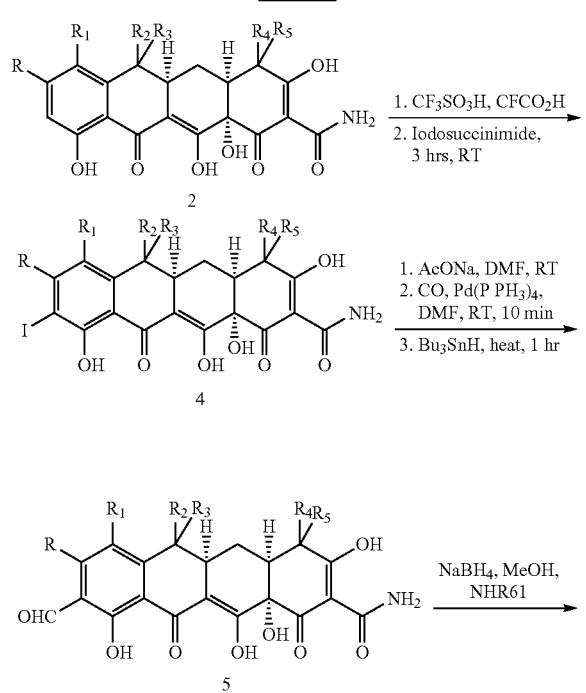

R6 = H, CO-alkyl, CONH-alkyl, CO2alkyl

Scheme 2.

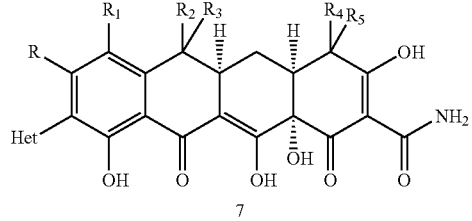

In Scheme 2, compound 4 is subjected to Suzuki reaction conditions by addition of the corresponding heteroaryl boronic acid (commercially available or prepared by the methods known to one familiar with the art) in DMF, and microwaved over a period of 1 min to afford after purification compound 7.

Scheme 3.

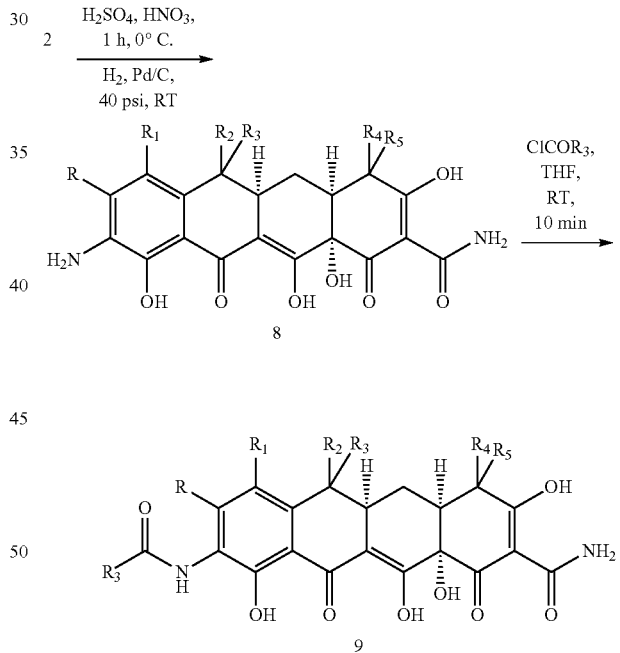

It should be noted that compound 2 is represented generically in Scheme 1 as having substituents at positions R7, R6 and R4, using the terminology of Formula A. By substituting appropriate groups for these substituents, one may obtain compounds defined by Formula A. A variety of compounds with the substituents of minocycline except at the 9-10 ring may be prepared as described herein, beginning with 9-aminominocycline, which is commercially available.

According to Scheme 1, compound 2 is treated with CF$_3$SO$_3$H in trifluoroacetic acid, followed by addition of iodosuccinimide over a period of 3 hrs at room temperature to get the iodo derivative that could be purified by chromatography to afford compound 4. (PCT Int. Appl. 2005009943, 3 Feb. 2005). Compound 4 is dissolved in DMF and treated with AcONA at room temperature, followed by addition of Pd(0) and Co gas. The resultant reaction mixture is stirred for 10 min at room temperature and then heated with Bu3SnH for a period of 1 hr to afford after filtration through a pad of silica gel an aldehyde derivative 5. Reductive amination of an appropriately substituted amine in methanol with sodium borohydride or alternatively reacting with appropriately substituted acyl chloride affords after chromatography compound 6.

In Scheme 3, treatment of compound 2 with a mixture of sulfuric and nitric acid at 0° C. over 1 hr affords the nitro intermediate that after purification is hydrogenated over Pd/C at room temperature at 40 psi to afford the amine compound 8 after chromatographic purification (Sum et al., "Synthesis and antibacterial activity of 9-substituted minocycline derivatives", BMCL, 16(2), 400-403, 2006). Reacting compound 8 with appropriately substituted acyl chloride in THF at room temperature over 10-30 min (PCT Int. Appl. No. 2006/130500, published 7 Dec. 2006) affords after chromatography compound 9.

Scheme 4.

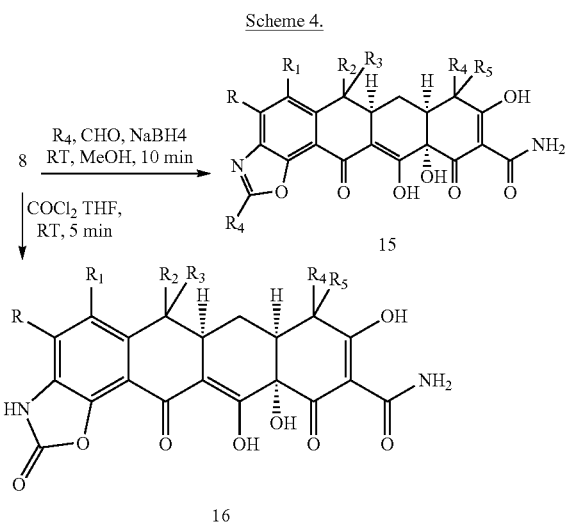

In Scheme 4, compound 8 is treated with appropriately substituted aldehyde in MeOH, followed by addition of sodium borohydride at room temperature over a period of 10 min to afford after chromatography compound 15.

Alternatively, treatment of compound 8 in THF with phosgene at room temperature for 5 min affords after purification compound 16.

Scheme 5.

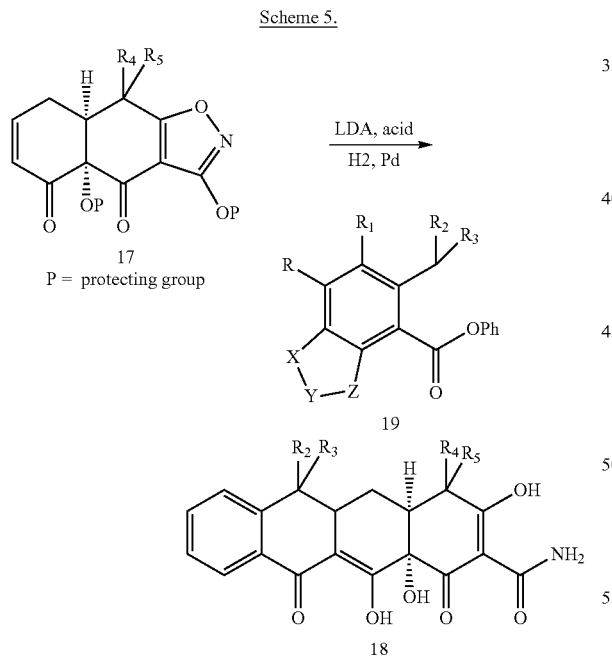

In Scheme 5, compound 17 is prepared following the procedure by M. Charest et al ("A Convergent Enantioselective Route to Structurally Diverse 6-Deoxytetracycline Antibiotics", Science, 2005, 308, p. 395-398). Treatment of 17 with appropriately functionalized 19 (pretreated with LDA in THF at low temperatures over 30 min), followed by the treatment with acid and a reduction procedure (H2, palladium) affords compound 18 after chromatography.

Scheme 6.

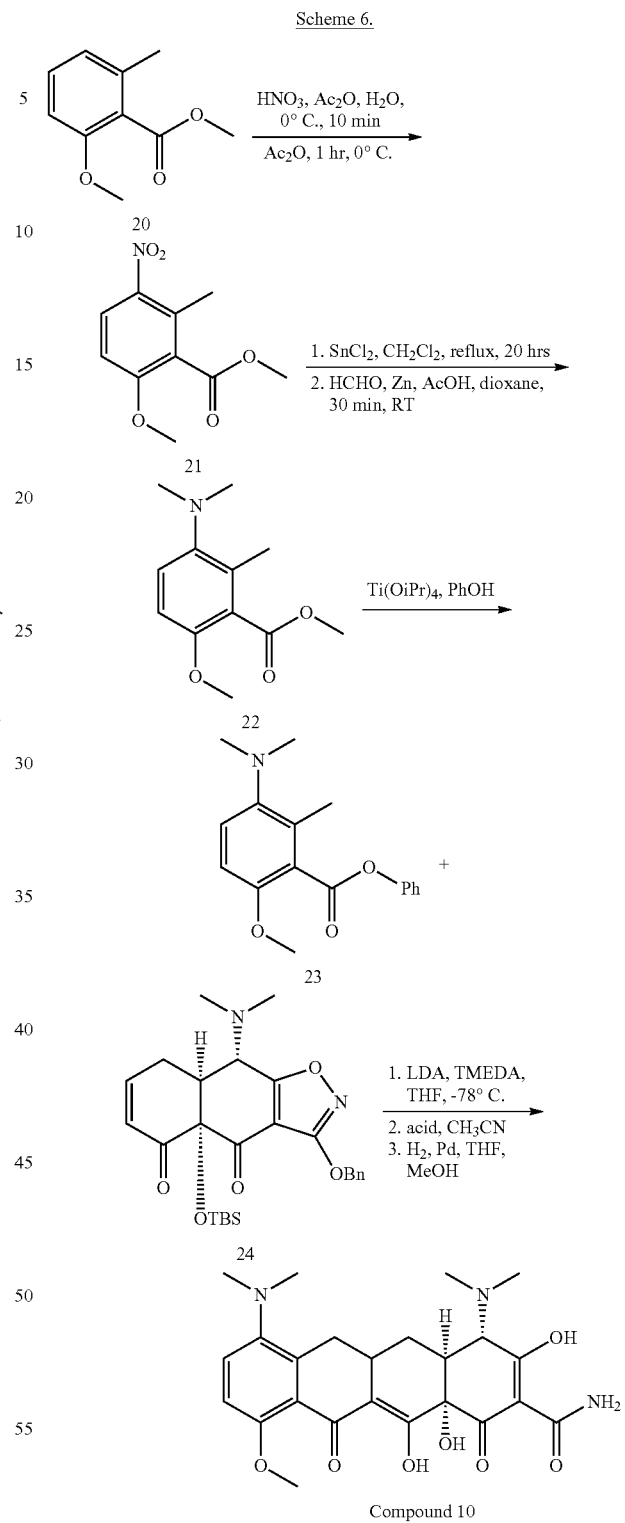

In Scheme 6, ethyl 2-Methoxy-6-methylbenzoate (20) is treated with nitric acid in acetic anhydride at 0° C. over 10 min. After 1 hr following work up procedure the nitro analog 21 (Mal et al., "Synthesis of chlorine-containing angucycline BE-23254 and its analogs" Tetrahedron 62(41), 2006, 9589) is subjected to the reaction with tin chloride in methylene chloride under reflux overnight to afford after filtration via pad of silica gel an amino intermediate. The amine is subjected to reductive amination with zinc in acetic acid in a presence of formaldehyde to afford after purification compound 22. Conversion to phenyl ester using the procedure described in Eur.Pat. Appl. 760359, published 5 Mar. 1997, affords 23. Treatment of 23 with an intermediate 24 (synthesis described in M. Charest et al, ("A Convergent Enantioselective Route to Structurally Diverse 6-Deoxytetracycline Antibiotics" Science, 2005, 308, p. 398) under established conditions affords the desired compound 10.

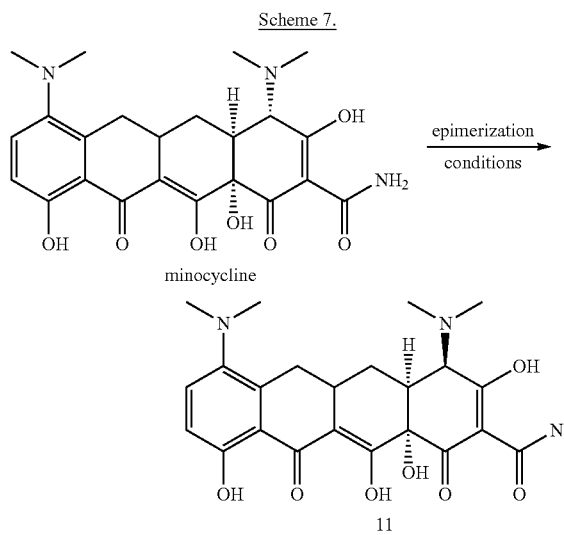

In Scheme 7, minocycline is epimerized to compound 11 under carefully monitored conditions by varying temperature, buffer system and pH (McCormick et al., "Studies of the Reversible Epimerization Occurring in the Tetracycline Family. The Preparation, Properties and Proof of Structure of Some 4-epi-Tetracyclines", *JACS*, 1957, 79, 2849). Additionally, compound 11 is also commercially available from various sources.

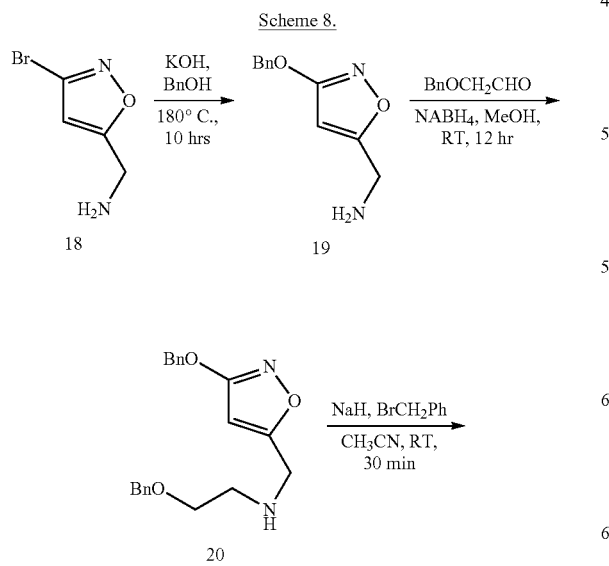

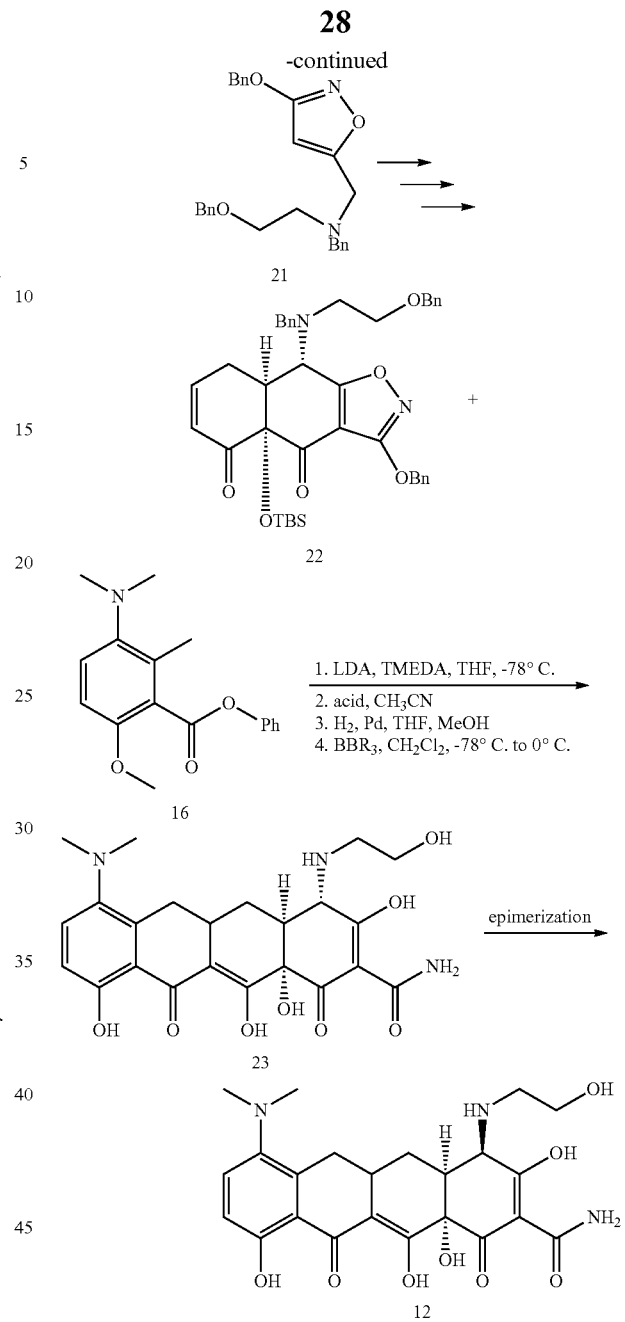

Scheme 8 shows a reaction from compound 18 to compound 19 with KOH, BnOH at 180° C. for 10 hrs. A reaction then from compound 19 to 20 uses BnOCH$_2$CHO, NaBH$_4$ and MeOH at room temp. for 1 hr. A reaction from compound 20 to 21 uses NaH, BrCH$_2$Ph, CH$_3$CN at room temp. for 30 min. Also, the scheme shows a reaction from compound 16 to 23 using LDA, TMEDA, THF at −78° C., then acid, CH$_3$CN, then H$_2$, Pd, THF, MeOH, then BBr$_2$ then CH$_2$Cl$_2$ 78° C. to 0° C.

In Scheme 8, starting from commercially available 3-Bomo-5Aminomethylisoxazole (25) under basic conditions in the presence of benzyl alcohol compound 26 is generated (CH 19641106). Treatment of 26 with benzyloxyacetaldehyde in methanol in the presence of sodium borohydride at RT over 1 hr affords intermediate 27. Reaction in acetonitrile with base (sodium hydride or others) and benzyl bromide at RT over 1 hr provides 28, which is subjected to conditions described in detail in Science, 2005, 308, p. 398 to afford compound 29. Compound 29 is reacted with an intermediate 23 by procedures described in the same Science paper to afford 30. Epimerization methods that yields epimer 12 may be established by those familiar with the art utilizing different pH, solvent and temperature conditions described in various papers for the tetracycline family (*Journal of Pharmacy and Pharmacology*, 1968, 20(7), 539).

methyl sulfoxide and protected with TBSOTf under mild basic conditions to afford compound 33. Compound 33 is coupled with 23 under the conditions described in Science, 2005, 308, p. 398 to afford final product 13 as a mixture of diastereomers that are separated by HPLC or flash chromatography.

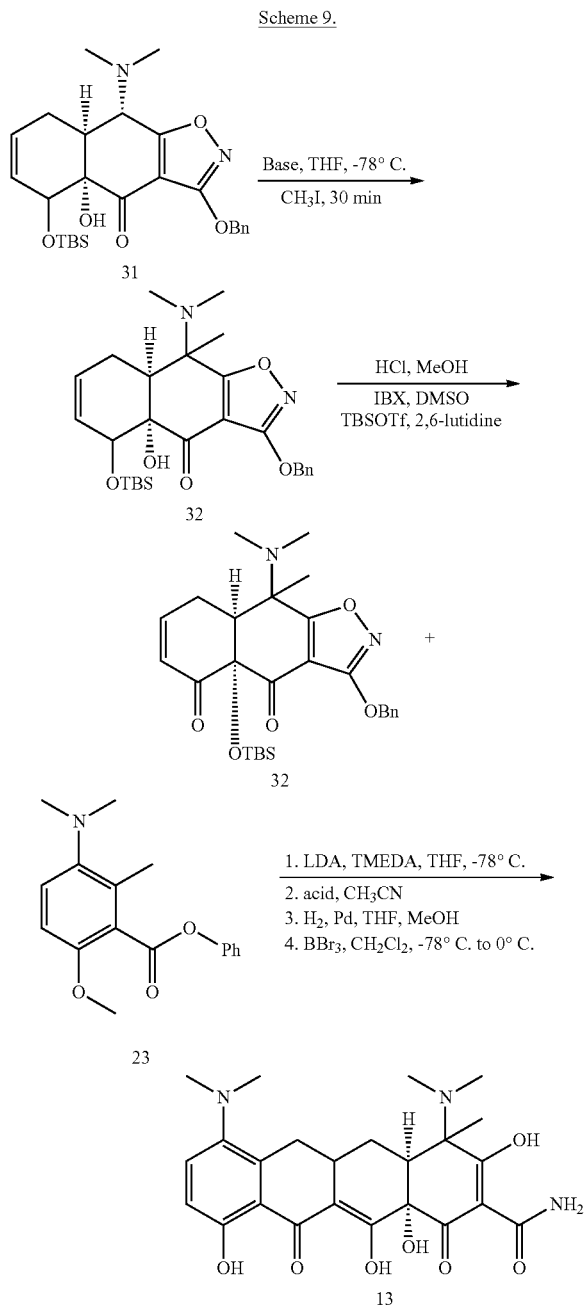

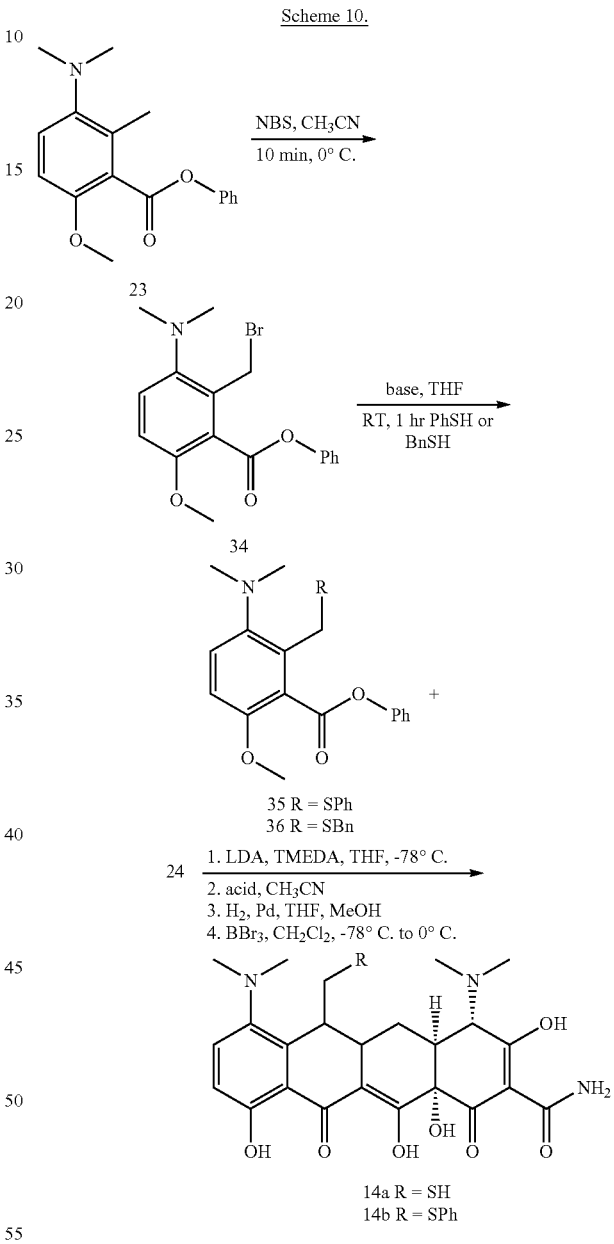

In Scheme 9, an intermediate 31 (synthesis described in Science, 2005, 308, p. 398) is treated with an appropriate base in THF at low temperature over 30 min and the reaction is quenched with 1 eq. of methyl iodide, to afford after work up 32 as a mixture of diastereomers. Compound 32 is treated with HCl in MeOH, following by oxidation with IBX in In Scheme 10, an intermediate 23 is treated with NBS in acetonitrile at 0° C. over 10 min to afford a bromo compound 34. 34 is treated with mild base in THF and either PhSH or BnSH to afford compound 35 or compound 36. Treatment of either 35 or 36 with 24 under conditions described in Science, 2005, 308, p. 398 affords the appropriate 14a or 14b.

As an example of synthetic methods creating a ring between positions R9 and R10, Scheme 11 is presented, which begins with compound 2 from Scheme 1.

Scheme 11.

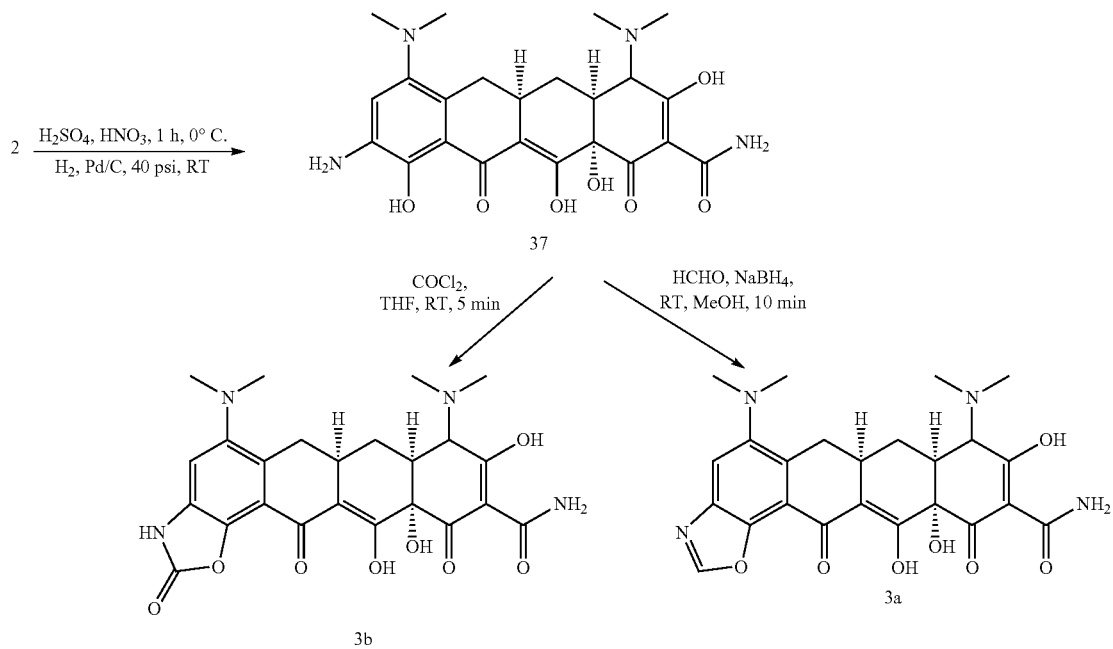

As shown in Scheme 11, compound 2 is treated with H$_2$SO$_4$, HNO$_3$ for 1 hr. at 0 degrees C. This is followed by H$_2$, Pd/C 40 psi at rt. Form compound 37 to 3b, reactions use COCl$_2$, THF, room temp. 5 min. From compound 37 to 3a, reactions use HCHO, NaBH4 at room temp. and MeOH for 10 min.

In Scheme 11, compound 37 is obtained from 2 (H2SO4, HNO3, 1 hr, 0° C.) and then treated with appropriately substituted aldehyde in MeOH, followed by addition of sodium borohydride at room temperature over a period of 10 min to afford after chromatography compound 3b.

Alternatively, treatment of compound 37 in THF with phosgene at room temperature for 5 min affords after purification compound 3a.

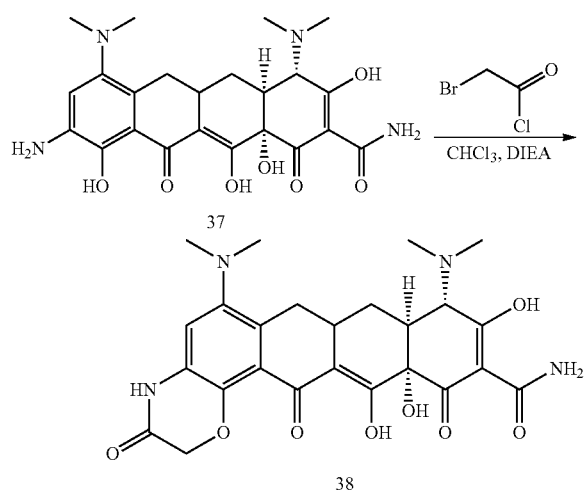

Scheme 12.

In Scheme 12, compound 38 is obtained from compound 37 (9-aminominocycline, commercially available or obtained from compound 2 as shown in Scheme 11) by treating compound 37 with bromoacetyl chloride and DIEA in CHCl$_3$. Purification of the resultant crude compound 38 by HPLC gives the TFA salt, which then is converted to its HCl salt by dissolving in 1M HCl/dioxane, followed by liophilization. This yields compound 38 as an HCl salt.

In Vitro Screening

A candidate compound designed and prepared as described above may be first tested in vitro to determine (a) antibiotic effect and (b) inhibition of cell cycle progression. As to antibiotic effect, this test is relatively straightforward and involves sensitivity of various microorganisms to the compound in comparison to a reference minocycline compound which is known to be antibiotic. As described above, the bacterial effect of minocycline compounds is known, and may be measured specifically, in addition to simple observation of inhibition of bacterial growth. That is, one may measure the effect of the candidate compound in preventing the attachment of aminoacyl tRNAs to the ribosomal acceptor (A) site. One may also use computational methods that model this interaction. In order to rule out antibacterial (and antiinfective) effects, one may screen against the following organisms: gram-negative bacteria (*N. gonorrhoeae, Haemophilus influenzae, Shigella* species, *Yersinia pestis, Brucella* species, *Vibrio cholera*); gram-positive bacteria (*Streptococcus pneumoniae, Streptococcus pyogenes*); mycoplasmas (*Mycoplasma pneumoniae, Mycoplasma fermentans* [inc. incognitis strain], *Mycoplasma penetrans*); others (*Bacillus anthracis* [anthrax], *Clostridium* species, *Chlamydia* species, *Actinomyces* species, *Entamoeba* species, *Treponema pallidum* [syphilis], *Plasmodium falciparum* [malaria] and *Borrelia* [Lyme] species).

As to cell cycle progression, in vitro and in vivo tests are described, e.g., in Satyanarayana et al., "DRF 3188 a novel semi-synthetic analog of andrographolide: cellular response to MCF 7 breast cancer cells," *BMC Cancer*, 2004; 4: 26. As described there, fluorescence associated cell-sorting analysis was conducted with MCF 7 cells treated with the candidate compound (5 µM) or reference compound (5 µM) for a period of 24 hours. Beckman Coulter also publishes instructions for fluorescence activated cell sorting in measuring cell cycle progression, in a publication entitled "Cell Cycle Analysis with Dual Measurement of Cyclin A2 Expression and DNA Content." Measurement of MAP kinase activity may be used, i.e., the candidate compound should inhibit MAP kinase in order to inhibit progression of the neuronal cell cycle. Such an assay is described in Yang et al., "MAP Kinase-Independent Signaling in Angiotensin II Regulation of Neuromodulation in SHR Neurons," *Hypertension*, 1998; 32:473481. As described there, neuronal cell lysates were prepared in the lysis buffer, and lysates were immunoprecipitated with anti-ERK2 antibody conjugated to agarose. Immunoprecipitates were electrophoresed and analyzed for P32 uptake. Further experimental protocols may be found in Alessi D R, Cuenda A, Cohen P, Dudley D T, Saltiel A R. "PD98059 is a specific inhibitor of the activation of mitogen-activated protein kinase in vitro and in vivo". *J Biol Chem.*, 1995; 270:27489-27494.

Another in vitro assay which may be used in evaluating the present compounds is inhibition of Poly(ADP-ribose) polymerase-1 (PARP-1). PARP-1 assays are used herein as an example of a measurement of a parameter that affects cell cycling. As reported in J. Biol. Chem, 10, 1074 (2002), Poly (ADP-ribose) Polymerase-1 (PARP-1) located in the nucleus is activated by DNA strand breaks during cellular genotoxic stress response and catalyses poly(ADPribosyl)ation of acceptor proteins. These acceptor proteins include those involved in modulation of chromatin structure, DNA synthesis, DNA repair, transcription, and cell cycle control. It is also known that PARP-1 enzymatic activity is induced by cellular oxidative stress mediated in part by mitochondrial enzymes, and that PARP-1 is directly inhibited by minocycline and other tetracycline derivatives. These agents have been evaluated by using cortical neuron cultures in which PARP-1 activation was induced by the genotoxic agents N-methyl-N'-nitro-N nitrosoguanidine (MNNG) or 3-morpholinosydnonimine (SIN-1). See, Alano et al., "Minocycline inhibits poly(ADP-ribose) polymerase-1 at nanomolar concentrations," Proc Natl Acad Sci USA. 2006 Jun. 20; 103(25): 9685-9690. Extensive PARP-1 activation as a result of oxidative and/or genotoxic stress can, in addition, lead to neuronal death through mechanisms linked to NAD+ depletion and release of apoptosis inducing factor from the mitochondria.

There is increasing recent evidence that restoring normal mitochondrial energy metabolism may be critical for the pathogenesis of many neurological diseases. See Castaldo et al, "Role of the mitochondrial sodium/calcium exchanger in neuronal physiology and in the pathogenesis of neurological diseases, Prog Neurobiol 2009 Jan. 12; 87 (1):58-79. Moreover, inhibition of PARP-1 has been observe to preserve neuronal energy metabolism, mitochondrial calcium cycling, attempted cell cycling, and apoptosis, and thus is likely to be critical for reducing some neuronal injuries. See Klaidman et al, "Recent developments in the role of mitochondria in poly (ADP ribose) polymerase inhibition" Curr Med Chem, 2003 Dec. 10 (24): 2669-78. Finally, a number of assays for PARP-1 assays are known and components for such assays are commercially available. For example, Trevigen offers a "standard" PARP purified to 50% purity and a high specific activity (HSA) enzyme purified to greater than 95%. The standard PARP enzyme is useful as a positive control for Western blot analysis of ribosylated proteins and PARP Activity Assays. The company's PARP Assay Kits measure incorporation of biotinylated Poly(ADP-ribose) onto histone proteins in 96-well plates. The assays allow screening of PARP inhibitors, measurement of PARP activity in cell and tissue extracts, and loss of PARP activity in cells undergoing apoptosis. Trevigen's Universal 96-well PARP Assay Kits measure the incorporation of biotinylated Poly (ADP-ribose) onto histone proteins in a 96 strip well format. These assays are ideal for the screening of PARP inhibitors and for measuring the activity of PARP in cell extracts. The colorimetric format (4677-096-K, 4676-096-K) measures sensitivity down to 10 m units of PARP per well, while the chemiluminescent format (4676-096-K, 4675096-K) measures sensitivity down to 2.5 m units of PARP per well. One may also measure inhibition of PARP cleavage to test the present compounds.

Cellular Assays

The present compounds may be further characterized by a number of cell-based assays. The assays described below may also be used to determine the initial effectiveness of a candidate compound.

Glutamate Challenge

Glutamate-induced neurotoxicity is an important contributing factor in chronic neurodegenerative diseases and in acute neuronal damages. In these diseases, there is an abnormal release of glutamate that contributes significantly to the neurological outcome. The released glutamate causes an excessive activation of glutamate receptors of the NMDA subtype, leading to an abnormal influx of Ca2+ rons and a subsequent neuronal death. Several kinase pathways, mainly including extracellular signal regulated-kinase (ERK) and p38 mitogenactivated protein kinase (MAPK) pathways have been demonstrated to be involved in glutamateinduced apoptosis and to be responsible for the downstream signals of overloading intracellular Ca2+. Assays may be performed as described in Li et al. "Novel Dimeric Acetylcholinesterase Inhibitor Bis(7)-tacrine, but Not Donepezil, Prevents Glutamate-induced Neuronal Apoptosis by Blocking N-Methyl-D-aspartate Receptors," *J. Biol. Chem.*, 280(18) (2005), and candidate compounds may be evaluated for their ability to prevent glutamate induced apoptosis.

Microglial Proliferation

Assays may be performed as described in Mander et al., "Microglia Proliferation Is Regulated by Hydrogen Peroxide from NADPH Oxidase," *The Journal of Immunology*, 2006, 176: 1046-1052. IL-1 and TNF-α are two cytokines released by microglia in response to infection, trauma, or neuronal damage in various CNS pathologies. It has been previously reported that IL-1 and TNF- can stimulate proliferation of microglia. In this assay, candidate compounds may be shown not to cause unwanted inflammatory activity, and to prevent inflammatory activity in the presence of stimulators, by a lack of microglial proliferation.

Oxidative Stress

Assays may be performed as described in Block et al., "Potent regulation of microglia-derived oxidative stress and dopaminergic neuron survival: substance P vs. dynorphin," The *FASEB Journal*. 2006; 20:251-258. In these assays, candidate compounds are tested for their ability to inhibit or not increase selective degeneration of dopaminergic (DA) neurons in the substantia nigra (SN). Increasing evidence has identified microglia as a predominant source of inflammation and oxidative stress contributing to DA neurodegeneration. In diseases such as Parkinson's disease it is known that in the disease state, microglia become overactivated and uncontrolled, resulting in either the initiation of DA neurotoxicity, or the amplification of DA cell death through reactive microgliosis. Briefly, extracellular superoxide (O2-) production from microglia is determined by measuring the superoxide dismutase (SOD) inhibitable reduction of 2-(4-lodophenyl)-3-(4-nitrophenyl)-5-(2,4,-disulfophenyl)-2Htetrazolium, monosodium salt, WST-1. The present compounds are selected on the basis of causing minimal production of superoxide.

Neuronal Protection Assays: Ischemic Stroke; Spinal Cord Injury

A number of cell-based assays which model cellular injury may also be employed. Widenfalk et al., "Neurotrophic Factors and Receptors in the Immature and Adult Spinal Cord after Mechanical Injury or Kainic Acid," *The Journal of Neuroscience*, May 15, 2001, 21(10):3457-3475 describe an assay which may be employed in testing the present compounds. In their work, injuries were inflicted on adult rats including weight-drop, transection, and excitotoxic kainic acid delivery; in newborn rats, partial transection was performed. The regulation of expression patterns in the adult spinal cord was compared with that in the PNS (peripheral nervous system) and the neonate spinal cord. After mechanical injury of the adult rat spinal cord, upregulations of NGF and GDNF mRNA occurred in meningeal cells adjacent to the lesion. BDNF and p75 mRNA increased in neurons, GDNF mRNA increased in astrocytes close to the lesion, and GFR-1 and truncated TrkB mRNA increased in astrocytes of degenerating white matter. Thus, one may measure the effect of one of the present compounds in upregulation of one of the factors which have been shown to be upregulated following injury, or one may simply measure the effect of the compound on damaged cells, as in Blesch A, Uy H S, Grill R J, Cheng J G, Patterson P H, Tuszynski M H (1999) "Leukemia inhibitory factor augments neurotrophin expression and corticospinal axon growth after adult CNS injury". *J Neurosci*, 19:3556-3566.

Assays for the present compounds in providing neuroprotection in ischemic stroke may be carried out. As described by Gladstone et al., "Toward wisdom from failure: lessons from neuroprotective stroke trials and new therapeutic directions," *Stroke*, 2002 August; 33(8):212336, preferred assays for assessment of therapeutic efficacy in preclinical studies should require, in addition to infarct size, demonstration of benefit on functional measures of motor, sensory, or cognitive deficits. Suitable assay conditions are described in Hara H, Friedlander R M, Gagliardini V, Ayata C, Fink K, Huang Z, Shimizu-Sasamata M, Yuan J, Moskowitz M A. "Inhibition of interleukin 1beta converting enzyme family proteases reduces ischemic and excitotoxic neuronal damage," *Proc Natl Acad Sci USA*, 1997; 94: 2007-2012. It is contemplated that the present compounds, when used as neuroprotectve agents in stroke, may be administered in conjunction with a thrombolytic agent.

In Vivo Testing

Preferably, once a candidate compound has been found to have substantially no antibiotic activity, to possess inhibition of cell cycle progression (either by actual measurement of DNA changes in a cell or by measurement of a cell cycle inducing biochemical event), (e.g., it prevents at least 50%, preferably at least 75%, of cells contacted from progressing to the next mitotic step), and/or to have satisfactory performance in the above-described cellular assays, it is tested in an animal model.

Penetration of the blood brain barrier may be assessed using the assay described in Example 6 below; other methods known in the art are also suitable.

Figure 2:
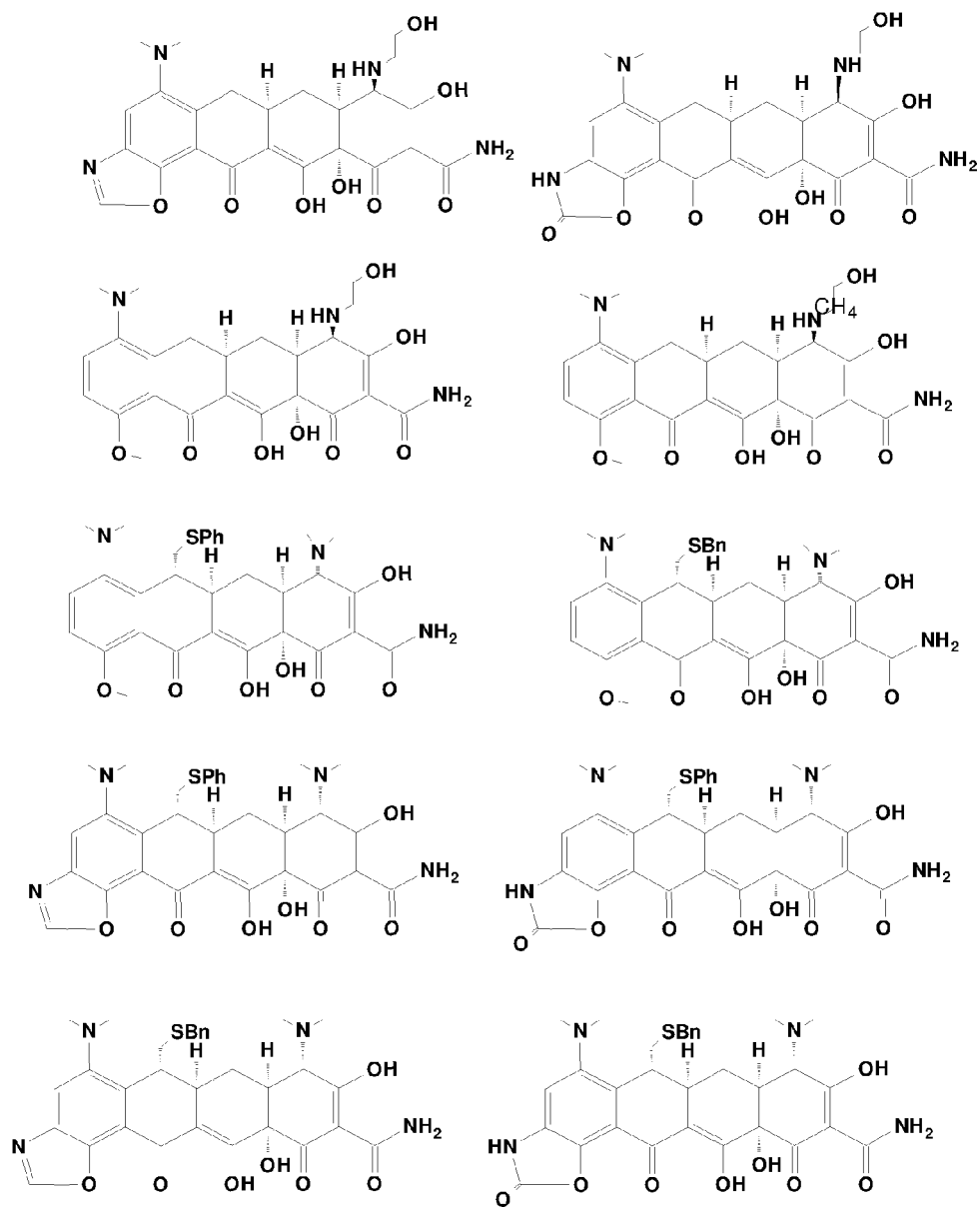
FIG. 2 also shows examples of compounds according to the present invention.

Neuronal damage may be tested by using any of a number of animal models of neuronal damage known in the art. For example, Shen et al., "The presenilin hypothesis of Alzheimer's disease: Evidence for a loss-of-function pathogenic mechanism," *Proc. Nat. Acad. Sci.*, Jan. 9, 2007, vol. 104, no. 2, pp: 403-409, describes conditional knockout mice in which presenilins (PSs) are selectively inactivated in the adult cerebral cortex. These mice develop agerelated, progressive neurodegeneration characterized by hallmarks of AD neuropathology, including synaptic loss, neuronal cell death, astrogliosis and tau hyperphosphorylation (See FIG. 2 of Shen et al., ibid). In these conditional mutant mice, inactivation of PS expression occurs at 4 weeks of age postnatally, and neurodegeneration becomes evident by 4 months of age. By the age of 9 months, 24% of cortical neurons and 35% of cortical volume are lost. Neurodegeneration is preceded by memory loss, synaptic plasticity impairments, reductions in NMDA receptor-mediated synaptic responses, and decreases in cAMP-response element (CRE)dependent gene expression (e.g., BDNF, c-fos), suggesting that these molecular defects mediate the subsequent neurodegeneration. Among mouse models of AD, conditional PS knockout mice are the only mutant mice derived from genetic manipulation of AD genes that reproduce the central features of AD, namely neurodegeneration and dementia.

U.S. Pat. No. 6,504,080 to Van Der Putten, issued Jan. 7, 2003, entitled "Transgenic animal model for neurodegenerative disorders," describes an animal model useful for testing potential therapeutic agents for the treatment of neurodegenerative disorders, in particular disorders associated with the presence of Lewy pathology. This method uses transgenic mice expressing a human α-synuclein A53T and a human α-synuclein wild-type transgene, under control of (mouse) Thy-1 regulatory sequences.

Formulation

The compounds of the present formulas, i.e., Formulas I, IA, A, AI 3A and 3B that are basic in nature are capable of forming a wide variety of salts with various inorganic and organic acids. The acids that may be used to prepare pharmaceutically acceptable acid addition salts of those compounds of Formulas I, IA, A, AI 3A and 3B that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Although such salts must be pharmaceutically acceptable for administration to mammals, it is often desirable in practice to initially isolate a compound of the Formulas I, IA, A, AI 3A and 3B from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of Formulas I, IA, A, AI 3A and 3B that are acidic in nature are capable of forming a wide variety of base salts. The chemical bases that may be used as reagents to prepare pharmaceutically acceptable base salts of those compounds of Formulas I, IA, A, AI 3A and 3B that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of compounds of the Formulas I, IA, A, AI 3A and 3B that are acidic in nature may be formed with pharmaceutically acceptable cations by conventional methods. Thus, these salts may be readily prepared by treating the compound of Formulas I, IA, A, AI 3A and 3B with an aqueous solution of the desired pharmaceutically acceptable cation and evaporating the resulting solution to dryness, preferably under reduced pressure. Alternatively, a lower alkyl alcohol solution of the compound of Formulas I, IA, A, AI 3A and 3B may be mixed with an alkoxide of the desired metal and the solution subsequently evaporated to dryness.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Administration

The present compounds may be delivered in various ways. In some embodiments, the compounds are given orally. In other embodiments, the compound is given in an enteric formulation. In further embodiments, the compound is delivered in an oral osmotic drug delivery device or transdermally with a patch. Transdermal delivery and formulation may be carried out, e.g., as described at U.S. Pat. No. 4,904,475 to Gale, et al., issued Feb. 27, 1990, entitled "Transdermal delivery of drugs from an aqueous reservoir," and at U.S. Pat. No. 5,656,286 to Miranda, et al., issued Aug. 12, 1997, entitled "Solubility parameter based drug delivery system and method for altering drug saturation concentration." Thus, the present compounds may be formulated for oral, intravenous, transdermal, inhalation, intranasal and other routes of administration as is known in the art.

In one embodiment, the compounds disclosed herein may be used as a treatment of a neurodegenerative disorder in a regimen comprising administration of 1 to 600 mg per day of a minocycline based compound as described (e.g., Formula I, A, 3A or 3B), wherein the composition may be administered alone or in combination with pharmaceutically acceptable carriers or diluents by any of the routes previously mentioned, and the administration may be carried out in single or multiple doses. The agent will preferably be derived from a minocycline scaffold but can be made from the scaffold of all compounds comprising the tetracycline class of compounds. The agent will have little or no antibiotic activity, will cross the blood brain barrier and will be anti-inflammatory. It will inhibit neuronal cell cycle progression.

The novel therapeutic agents of this invention can be administered advantageously in a wide variety of different dosage forms, i.e., they may be combined with various pharmaceutically acceptable inert carriers in the form of tablets, capsules, skin patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored or made to extend bioavailability over an extended time (time release). In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compound could also be formulated as an acid addition salt, e.g., a quaternary ammonium salt. The salt is generally formed by contacting the compound with a mineral or an organic acid. When the compounds are given orally, it is generally preferred that they have a bioavailability that is greater than about 15%, more preferably greater than about 20% of the administered dose.

For parenteral administration (including intraperitoneal, subcutaneous, intravenous, transdermal, intradermal or intramuscular injection), solutions of a therapeutic compound of the present invention in either sesame or peanut oil or in aqueous propylene glycol may be employed. The aqueous solutions should be suitably buffered (preferably pH less than 8 or 3.5-7.5) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables. Preferably, the compounds have high lipophilicity so they can cross the blood brain barrier.

Clinical Applications

A common feature of many neurological and retinal diseases is neurodegeneration resulting from the inappropriate activation of the cell-suicide process known as apoptosis, also known as programmed cell death. Neuronal apoptosis is an essential feature of nervous system development, since half of all neurons produced during development die before maturation, and survival of mature neurons is dependent upon their use and electrical activity.

While properly regulated apoptosis is an essential feature of normal nervous system development and function, numerous studies show that it also occurs in a wide variety of neurological diseases, including neurodegenerative diseases, ischemic stroke, traumatic brain injury, and following exposure to chemical or biological toxins. Retinal neurological diseases are also influenced by many of these factors.

Current data show that the molecular mechanisms involved in neuropathological degeneration are similar to those that regulate normal neuronal apoptosis during development. The control of apoptosis in both normal and pathological conditions is regulated by a multitude of molecules, including the caspases, Bcl-2 proteins, apoptosis inducing factor, endonuclease G, p38 and other mitogen activated protein kinases, JNK, cyclin dependent kinases, p53 and related proteins, glyceraldehyde 3-phosphate dehydrogenase, and inducible nitric oxide synthase.

Just as there have been many pro-apoptotic molecules identified, so have there been numerous anti-apoptotic molecules and signal transduction pathways identified, i.e., molecules and pathways that promote neuronal survival. Neuronal apoptosis is inhibited, and neuronal survival is promoted, by numerous endogenous neurotrophic proteins. Neuronal apoptosis is also inhibited by neuronal electrical activity.

The PI-3K/Akt pathway has been the best studied of these pro-survival pathways, although the Raf-MEK-ERK pathway has also been studied and characterized as an important neuronal survival pathway. It has been shown for both central and peripheral neurons that the pro-survival effects of nerve growth factor, insulin-like growth factor-1, and brain derived neurotrophic factor are dependent upon activation of the PI-3K/Akt pathway. When the PI3K/Akt pro-survival pathway is activated by these and other molecules, pro-apoptotic proteins, including Bcl-2 and JNK and others, are directly targeted and inactivated, while other proapoptotic proteins are inactivated by other indirect means Like PI-3K/Akt, the Raf-MEK-ERK pathway also promotes neuronal survival by multiple mechanisms, including direct inactivation of pro-apoptotic factors.

There exists much evidence, therefore, that there exists a final common pathway responsible for many neurological and retinal diseases, and that this final common pathological pathway can be attenuated or eliminated by induction of pro-survival pathways. Furthermore there exists much evidence that this final common pathway exists irrespective of the initial neuronal insult, i.e., irrespective of whether pro-apoptotic pathways are initiated because of hypoxia or anoxia (ischemic stroke, emboli, vascular dementia, post coronary-artery bypass grafting cognitive decline), mechanical stress (traumatic brain injury, spinal cord injury), abnormal protein expression (Huntington's disease), autoimmunity (multiple sclerosis), oxidative stress (Alzheimer's disease), intraocular pressure (glaucoma), glucose toxicity and insulin deprivation (diabetic retinopathy), etc.

The inventive compounds are structurally related to molecules known to effect neuroprotection and retinoprotetion in a very wide range of diseases through activation of prosurvival pathways and attenuation or elimination of pro-apoptotic pathways. This class of molecules has been shown, as summarized in part by Yong et al "The Promise of Minocycline in Neurology" in the journal *Lancet Neur.* issue #204, Vol. 3, pp. 764-51, to be neuroprotective in both in vitro and in animal models of ischemic and hemorrhagic stroke, Parkinson's disease, Huntington's disease, multiple sclerosis spinal crush injury, and amyotrophic lateral sclerosis. Data from clinical studies show this class of molecules to be protective in Alzheimer's disease and acute stroke, as summarized in publications by Loeb et al in "A Randomized Controlled trial of Doxycycline and Rifampin for Patient's with Alzheimer's Disease"; *The American Geriatrics Soc.,* 2004; 2: 381-387, and Lampl et al in "Minocycline treatment in acute stroke: an open-label evaluator-blinded study" *American Academy of Neurology;* 2007; 69; pp. 1404-1410. Molecular studies, as described by Chong et al (Activating Akt and the Brain's Resources to Drive Cellular Survival and Prevent Inflammatory Injury; *Histol Histopathol.,* 2005; 20 (1) pp. 299-315) show that this class of neuroprotective molecules inhibits the production and pro-apoptotic effects of caspases, p38MAP kinase, and inducible nitric oxide synthase, among other molecules, and promotes the strong pro-survival effects through induction of the PI-38/akt pathway.

That these molecules are effective in such a wide-ranging array of diseases through mechanisms known to operate in both normal and pathological conditions supports two fundamental ideas emerging in neurology, namely a) that there exists a final common proapoptotic pathway for a wide range of diseases resulting in neurodegeneration and neuropathology that is closely tied to neuronal cell cycling, and b) that new treatment paradigms for these diseases can be effected by activating pro-survival neuroprotective pathways that counter these pathological effects in part through inhibition of neuronal cell cycling, regardless of the initiating pathological insult.

The present compounds may be determined to have in vivo efficacy in humans by known clinical research techniques. Clinical research may be combined with biomarkers, e.g., testing limited to Alzheimer's patients lacking apoE4. Exemplary clinical trial designs are outlined at clinical trials.gov. For example, a current study of bapineuzumab in patients with mild to moderate Alzheimer's Disease may be modified for study of a compound according to the present invention, taking in to account the differences between antibody therapy (antibody to beta-amyloid) and the current small molecules. It is anticipated that the present compounds will prevent the formation of beta-amyloid.

EXAMPLES

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to those described below. The reactions are performed in a solvent appropriate to the reagents and materials employed and suitable for the transformations being affected.

Example 1: Synthesis of Compound 38

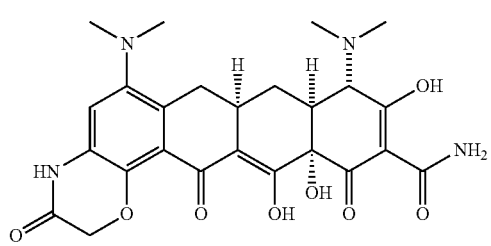

9-Amino minocycline HCl (37, 509 mg, 1 mmol, 1.0 eq) was dissolved in mixture CHCl3 (12 ml, amylene stabilized) and the resulting solution was treated with DIEA (0.524 ml, 3.0 mmol, 3.0 eq) and cooled in an ice bath. Bromoacetyl chloride (0.91 ml, 1.1 mol, 1.1 eq) was added dropwise and the resulting reaction mixture was stirred for 4 h at ambient temperature. LC-MS analysis indicated compound 2 as a main product with some impurities. The reaction mixture was diluted with CHCl$_3$ (50 mL), washed with H2O (2×50 mL) and dried over anhydrous Na2SO4. LC-MS analysis of both CHCl$_3$ and aqueous layers showed predominant conversion to compound 38. CHCl$_3$ layer was concentrated down and the resultant residue was dissolved in 4 mL of DMSO. Purification of the crude product by HPLC provided 72 mg of the target product as a yellow solid (TFA salt). The product was converted to its HCL salt by dissolving in 1M HCl/Dioxane, followed by liophilization to provide 38 as HCl salt. LC/MS analysis m/z 513.2 [M+H]$^+$.

Example 2: Synthesis of Compound 3b

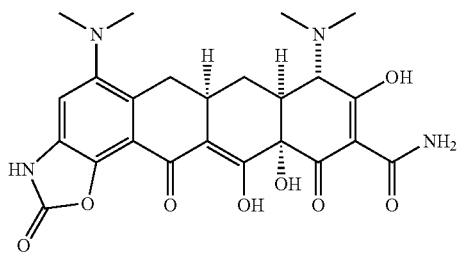

100 ml round bottom flask was charged with 9-aminominocycline HCl (37, 2 grams, 80% pure by HPLC at 254 nm) followed by dichloromethane (40 ml). The resultant suspension was treated with CDI (500 mg, 1.0 eq) in 4 ml of DMSO over 1 hour. LC-MS analysis of the resulting dark brown reaction mixture indicated disappearance of starting material and a major product with the expected mass for 3b. The reaction mixture was evaporated to dryness under reduced pressure to give a brownish/black oil which was dissolved in 4 ml of DMSO and then purified by reverse phase preparative HPLC (0.1% TFA buffer/acetonitrile, 50 ml/min over 60 minutes). The obtained mixed fraction containing 3b was liophilized and re-chromatographed by reverse phase HPLC (0.1% formic acid buffer, 50 ml/min over 60 minutes). Pure fractions were pooled to give, after liophilization, 280 mg of >95% of pure 3b as a formate salt. The material was consequently dissolved in 5 ml of 1M HCl dioxane and then liophilized to provide 3b HCl salt as an off-white solid (230 mg). LC/MS analysis m/z 499.1 [M+H]$^+$.

Example 3: Synthesis of Compound 3a

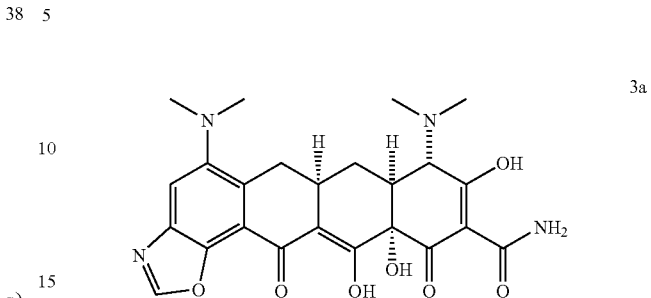

A 50 ml round bottom flask was charged with 9-aminominocycline HCl (37, 230 mg) followed by addition of MeOH (20 ml) and triethylorthoformate (80 eq). The resultant reaction mixture was heated to 50° C. After one hour, LC-MS analysis indicated a complete consumption of starting material and a major peak matching the expected mass of the product. The solvent was evaporated under reduced pressure to give a yellow oil which was dissolved in 3 ml of DMSO and purified by reverse phase HPLC (0.1% TFA buffer/acetonitrile, 50 ml/min over 60 minutes). The purified fractions were pooled and liophilized to give 3a TFA salt as an off-white solid. The material was dissolved in 5 ml of 1M HCl/dioxane and then liophilized to give 3a HCl salt as an off-white solid (76 mg). LC/MS analysis m/z 482.1[M+H]+.

Example 4: Antimicrobial Susceptibility Test

Anti-microbial susceptibility (zone of inhibition) tests were conducted by an outside analytical laboratory. The Kirby-Bauer or disc diffusion method of assessing antimicrobial activity is an established literature procedure and was used with some modifications to the standard protocol: 1) *S. Aureus* and *E. Coli* were grown in Muller-Hinton broth and incubated at 30-35° C. for 18-24 hrs, 2) samples were diluted in sterile water for injections or pure water to achieve a concentration of 30 ug/ml and were plated in triplicate, and 3) the test plates were prepared using Muller-Hinton agar and incubated at 30-35° C. for approximately 24 hrs.

The diameters of the zone of inhibition (if present) around the test sample were measured using calibrated calipers. As shown in Table 2, Compounds 3b and 38 demonstrated no antimicrobial activity in this assay (i.e., were substantially not antibiotic). 3a has some activity (average zone of 24.45 mm) against *S. Aureus*.

TABLE 2

| Sample ID | The diameter of the zone including sample |
|---|---|
| 3a (*S. Aureus*) | 24.45 mm (average) |
| 3a (*E. Coli*) | no zone |
| 3b (*S. Aureus*) | no zone |
| 3b (*E. Coli*) | no zone |
| 38 (*S. Aureus*) | no zone |
| 38 (*E. Coli*) | no zone |

Example 5: Poly(ADP-Ribose) Polymerase (PARP) Inhibition Assay

Exemplary compounds of the present invention were assayed for inhibitory activity on cell-cycle progression using a PARP assay. The assay was run by an outside analytical laboratory using the standard chemiluminescent PARP inhibition protocol. In addition to the standard controls utilized in this assay, a standard solution of 30 μg minocycline was used as an internal positive control for the test compounds, with the control samples being plated in triplicate.

Figure 3:
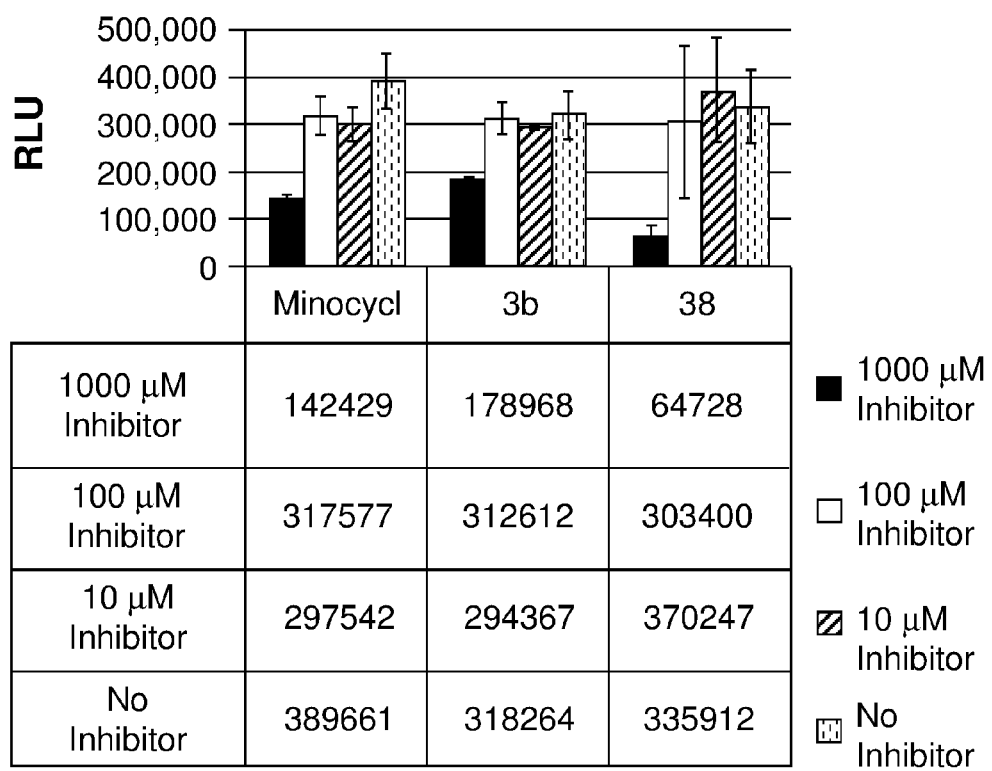
FIG. 3 shows the results of a chemiluminescent PARP inhibition assay performed for exemplary embodiments of the present invention.

As shown in FIG. 3, compounds 3a and 38 demonstrated PARP inhibitor activity similar to minocycline. FIG. 3 presents the data of the PARP inhibition for minocycline, 3b (NSN1885) and 38 (NSN19203) at 10,100 and 1000 uM inhibitor concentrations. Data were generated using HT Universal Chemiluminescent PARP Assay kit, with Histone-coated Strip Wells, from Trevigen.

Example 6: Intravenous Blood Brain Barrier (BBB) Penetration Assay

Protocol

Intravenous blood brain barrier (BBB) penetration of Compounds 38 and 3b in mice was assessed by an outside analytical laboratory using the standard protocol. CD-1 mice were tail-vein injected with 38 or 3b (1 mg/kg, n=3), and the plasma and brain samples were collected at 30, 60 and 180 min time intervals. The concentration of 38 and 3b in brain (ng/g tissue), plasma and the ratio of the brain concentration at each time point were determined by acetonitrile precipitation of the test compounds from the samples followed by HPLC-MS?MS analysis.

After treatment of the animals with the test compounds, plasma samples were collected by cardiac puncture. Blood aliquots (300-400 μL) were collected in lithium heparin-coated tubes, mixed gently, then kept on ice and centrifuged at 2,500×g for 15 minutes at 4° C. within 1 hour of collection. Plasma was then harvested and kept frozen at −20° C. until further processing.

Immediately after blood sampling, mice were decapitated and the whole brains were quickly removed, rinsed with cold saline (0.9% NaCl, g/mL), surface vasculature ruptured, blotted with dry gauze weighed and kept on ice until further processing within 1 hour of collection. Each brain was homogenized in 1.5 mL cold phosphate-buffered saline, pH 7.4, for 10 seconds on ice using a POWERGEN 125 homogenizer. Each sample was then stored at −20° C. until further processing.

Brain homogenates collected as above were processed by adding an equal volume of chilled 26% (g/mL) neutral Dextran (average MW 65,000-85,000, from Sigma, catalog number D-1390) solution to obtain a final Dextran concentration of 13%. The homogenate was centrifuged at 5400×g for 15 minutes at 4° C. Supernatents were subsequently processed using acetonitrile precipitation and analyzed by HPLC-MS. A brain calibration curve was generated by spiking drug-free brain homogenate from the control animals with test compound at specified concentration levels. The spiked brain homogenate samples were processed together with the unknowns using the same procedure. Processed brain samples were stored frozen (−20° C.) until LC-MS/MS analysis.

Plasma samples collected as above were processed and analyzed as for the brain homogenate supernatents described above.

After processing, all samples were analyzed using HPLC-MS/MS analysis. HPLC analysis employed a Synergi Max-RP 80 HPLC column (2×50 mm, 4 μm, Phenomenex Part No. 00B-4337-B0), using a first mobile phase of 13.3 mM ammonium formate/6.7 mM formic acid in water, and a second mobile phase of 6 mM ammonium formate/3 mM formic acid in water/CH$_3$CN (1/9, v/v). MS/MS analysis was done on a TSQ QUANTUM with selected reaction monitoring, positive ion mode, using a capillary temperature of 325° C. and a capillary voltage of 4.0 kV. Peak areas were recorded, and the concentrations of the test compound in the unknown brain samples were determined using the respective calibration curves.

Results

The concentrations of Compound 3b in the brain after 30, 60 and 180 min were correspondingly 6.7 ng/g (SE 0.2), 5.8 ng/g (SE 0.5) and "below the limit of quantitation". Plasma concentrations at 30, 60 and 180 min were correspondingly 97 ng/ml (SE 10), 27 ng/ml (SE 2) and 4 ng/ml (SE 1). Calculated ratios of brain to plasma concentration of 3b after 30, 60 and 180 min were correspondingly 0.07 (SE 0.01), 022 (SE=0.02) and NC (not calculable).

Thus, it was shown that Compound 3b exhibits acceptable blood brain barrier penetration in vivo.

Example 7: Stability Testing

Compounds of the present invention will be stable in solution and/or in powder form. To test for stability in different solutions (e.g., de-ionized water, de-ionized water adjusted with K$_2$HPO$_4$ to pH 7.4, de-ionized water adjusted with NaOH to pH 9, saline solution or PBS). The compounds are tested for degradation at different times at different temperatures. By way of example, compound 3b was stable in de-ionized water saline and PBS at pH of about 3 to 7.5.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A compound having the formula:

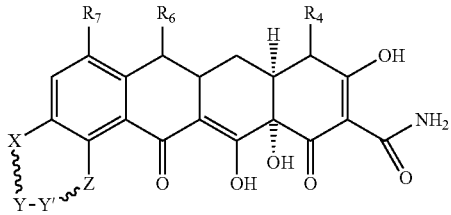

wherein $R_4$, $R_6$, $R_7$, X, Y, Y' and Z are defined as follows:
$R_4$, $R_6$, and $R_7$ are each independently selected from the group consisting of H, $C_{1-10}$ alkyl, $C_{1-10}$ alkenyl, $C_{1-10}$ alkynyl, $C_{5-10}$ alkyl ring, $C_{5-10}$ aryl ring, —C(=O)R$^{1a}$, —NR$^{1a}$R$^{1a}$, —SR$^{1a}$R$^{1a}$, OH, and OR$^{1a}$R$^{1a}$;

X and Z are each independently selected from the group consisting of —$CR^{1a}R^{1a}$—, —$CR^{1a}(OH)$—, —$C(=O)$—, —O—, —$NR^{1a}$—, and —S—;

Y and Y' taken together form a structure selected from the group consisting of —$C(=O)C(R^{1a}R^{1a})$— and —$C(R^{1a}R^{1a})C(=O)C(R^{1a}R^{1a})$—; and $R^{1a}$ is independently selected from the group consisting of H and $C_{1-10}$ alkyl;

or a pharmaceutically acceptable salt thereof.

2. The compound of claim 1, wherein —X—Y—Y'—Z— is —NH—C(=O)—$CH_2$—O—.

3. The compound of claim 1, wherein $R_4$ is —$NR^{1a}R^{1a}$.

4. The compound of claim 1, wherein $R_7$ is —$NR^{1a}R^{1a}$.

5. The compound of claim 3, wherein $R_7$ is —$NR^{1a}R^{1a}$.

6. The compound of claim 1, wherein $R_7$ is —N—$(CH_3)_2$.

7. The compound of claim 1, wherein $R_6$ is selected from the group consisting of H and $C_{1-10}$ alkyl.

8. The compound of claim 1, wherein $R_4$, $R_6$, and $R_7$ are each independently selected from the group consisting of H, OH, and $C_{1-10}$ alkyl, wherein said $C_{1-10}$ alkyl is optionally substituted with up to three amine or hydroxyl groups.

9. The compound of claim 1, wherein $R_6$ is H and $R_4$ and $R_7$ are each —N—$(CH_3)_2$.

10. The compound of claim 1, wherein X is amino and Z is —O—.

11. The compound of claim 9, wherein X is amino and Z is —O—.

12. The compound of claim 1, wherein the compound is an up epimer at $R_4$.

13. The compound of claim 9, wherein the compound is an up epimer at $R_4$.

14. The compound of claim 1, wherein X is —NH—.

15. The compound of claim 9, wherein X is —NH—.

16. The compound of claim 1, wherein Z is —O—.

17. The compound of claim 9, wherein Z is —O—.

18. The compound of claim 1, wherein Y and Y' taken together form the structure —$C(=O)C(R^{1a}R^{1a})$—.

19. The compound of claim 9, wherein Y and Y' taken together form the structure —$C(=O)C(R^{1a}R^{1a})$—.

20. A composition comprising:
a compound according to claim 1, and
a pharmaceutically acceptable carrier.

* * * * *